United States Patent
Minagawa et al.

(10) Patent No.: US 11,236,342 B2
(45) Date of Patent: Feb. 1, 2022

(54) SECRETORY IMMUNOGLOBULIN A (SIGA)-BINDING NUCLEIC ACID MOLECULE, SIGA ANALYSIS SENSOR, AND SIGA ANALYSIS METHOD

(71) Applicants: NEC Solution Innovators, Ltd., Tokyo (JP); NATIONAL UNIVERSITY CORPORATION GUNMA UNIVERSITY, Gunma (JP)

(72) Inventors: Hirotaka Minagawa, Tokyo (JP); Katsunori Horii, Tokyo (JP); Jou Akitomi, Tokyo (JP); Naoto Kaneko, Tokyo (JP); Iwao Waga, Tokyo (JP); Masayasu Kuwahara, Maebashi (JP)

(73) Assignees: NEC Solution Innovators, Ltd., Tokyo (JP); NATIONAL UNIVERSITY CORPORATION GUNMA UNIVERSITY, Maebashi (JP)

( * ) Notice: Subject to any disclaimer, the term of this patent is extended or adjusted under 35 U.S.C. 154(b) by 284 days.

(21) Appl. No.: 16/333,293

(22) PCT Filed: Apr. 20, 2017

(86) PCT No.: PCT/JP2017/015934
§ 371 (c)(1),
(2) Date: Mar. 14, 2019

(87) PCT Pub. No.: WO2018/051569
PCT Pub. Date: Mar. 22, 2018

(65) Prior Publication Data
US 2019/0241895 A1 Aug. 8, 2019

(30) Foreign Application Priority Data
Sep. 15, 2016 (JP) .............................. JP2016-180892

(51) Int. Cl.
| C12N 15/115 | (2010.01) |
| C12Q 1/68 | (2018.01) |
| G01N 33/53 | (2006.01) |
| C12N 15/09 | (2006.01) |

(52) U.S. Cl.
CPC ............ *C12N 15/115* (2013.01); *C12N 15/09* (2013.01); *C12Q 1/68* (2013.01); *G01N 33/53* (2013.01); *C12N 2310/16* (2013.01); *C12N 2310/333* (2013.01); *C12N 2310/335* (2013.01); *C12N 2310/336* (2013.01)

(58) Field of Classification Search
None
See application file for complete search history.

(56) References Cited

U.S. PATENT DOCUMENTS

2016/0311845 A1 10/2016 Kuwahara

FOREIGN PATENT DOCUMENTS

| CN | 105738633 A | 7/2016 |
| JP | 10-239312 A | 9/1998 |
| JP | 10-274654 A | 10/1998 |
| JP | 2013-40118 A | 2/2013 |
| JP | 2016-56136 A | 4/2016 |
| WO | 2015/064223 A1 | 5/2015 |

OTHER PUBLICATIONS

Tokiko Isowa, "Relationship between Job Stressor, Burnout and Physical Health Problem in Nurses: A Study Using Questionnaire and Immunological Parameter", Japanese Journal of Behavioral Medicine, 2003, pp. 25-33, vol. 10, No. 1.
Yuri Imaizumi, et al., "Efficacy of Base-Modification on Target Binding of Small Molecule DNA Aptamers", Journal of the American Chemical Society., 2013, pp. 9412-9419, vol. 135, No. 25.
Masayasu Kuwahara, "Creation of Nucleic Acid Aptamers that Contain Unnatural Nucleotides", Polymers, Oct. 2014, pp. 730-731, vol. 63, No. 10.
Masayasu Kuwahara, et al., "Modified nucleic acid aptamer selections using capillary electrophoresis", Electrophoresis Letters, 2015, pp. 88-90, vol. 59, No. 2.
Naoto Honda, et al., "Selection of VEGF-binding DNA aptamers with Base Modifications Using a CE-SELEX method", The 95th Spring Annual Meeting of Chemical Society of Japan 2015 Abstracts III, 2015, p. 877, 2 J5-02.
Masako Hasegawa-Ohira, et al., "Change in the Secretion of Salivary Cortisol, Immunoglobulin A, and Alpha-amylase while Asleep", Transactions of Japanese Society for Medical and Biological Engineering, 2011, pp. 798-804, vol. 49, No. 6.
Yoshihide Tanaka, et al., "Biomarkers of stress and fatigue", Folia Pharmacol. Jpn., 2011, pp. 185-188, vol. 137.
Shin-ichi Wakida, et al., "Research on stress measurement biochip for a single drop of saliva", Folia Pharmacol. Jpn., 2013, pp. 296-301, vol. 141.
International Search Report for PCT/JP2017/015934 dated Jul. 18, 2017 [PCT/ISA/210].
Communication dated Jan. 30, 2020, from the Japanese Patent Office in application No. 2018-539512.
Kasahara et al., "Capillary Electrophoresis-Systematic Evolution of Ligands by Exponential Enrichment Selection of Base- and Sugar-Modified DNA Aptamers: Target Binding Dominated by 2'-O,4'-C-Methylene-Bridged/Locked Nucleic Acid Primer", Analytical Chemistry, vol. 85, No. 10, pp. 4961-4967, 2013 (7 pages total).
Extended European Search Report dated Jul. 10, 2020, from the European Patent Office in Application No. 17850476.7.

(Continued)

*Primary Examiner* — Sean McGarry
(74) *Attorney, Agent, or Firm* — Sughrue Mion, PLLC

(57) ABSTRACT

The present invention provides a novel molecule that can be used for detection of sIgA. The sIgA-binding nucleic acid molecule of the present invention is characterized in that it binds to secretory immunoglobulin A (sIgA) with a dissociation constant of 37.7 nM or less, and preferably includes a polynucleotide consisting of any of base sequences of SEQ ID NOs: 1 to 12 or a partial sequence thereof, for example. According to the sIgA-binding nucleic acid molecule of the present invention, it is possible to detect sIgA in saliva.

19 Claims, 6 Drawing Sheets
Specification includes a Sequence Listing.

(56) References Cited

OTHER PUBLICATIONS

Kasahara, "Development of the convenient method for artificial nucleic acid aptamer preparations using CE-SELEX", Mar. 25, 2014, XP 55674545, Retrieved from the Internet: URL:https://gair.media.gunma-u.ac.jp/dspace/bitstream/10087/8646/1/e-k0474-3.pdf, 117 pages total.
Vorobyeva et al., "Aptamers Against Immunologic Targets: Diagnostic and Therapeutic Prospects", Nucleic Acid Therapeutics, vol. 26, No. 1, Feb. 4, 2016, XP 055352538, 14 pages total.
Oortwijn et al., "A pathogenic role for secretory IgA in IgA nephropathy", Kidney International, vol. 69, No. 7, pp. 1131-1138, XP 55674536, Jan. 4, 2006, 8 pages total.
Kasahara et al., "Artificial Specific Binders Directly Recovered from Chemically Modified Nucleic Acid Libraries", Journal of Nucleic Acids, vol. 2012, Article ID 156482, pp. 1-13, XP 55674671, Oct. 8, 2012, 14 pages total.
Minagawa et al., "Fluorescence Polarization-Based Rapid Detection System for Salivary Biomarkers Using Modified DNA Aptamers Containing Base-Appended Bases", Analytical Chemistry, vol. 92, No. 2, pp. 1780-1787, XP 55674810, Dec. 19, 2019, 8 pages total.
Partial Supplementary European Search Report dated Mar. 23, 2020, from the European Patent Office in Application No. 17850476.7.

SECRETORY IMMUNOGLOBULIN A (SIGA)-BINDING NUCLEIC ACID MOLECULE, SIGA ANALYSIS SENSOR, AND SIGA ANALYSIS METHOD

CROSS REFERENCE TO RELATED APPLICATIONS

This application is a National Stage of International Application No. PCT/JP2017/015934, filed on Apr. 20, 2017, which claims priority from Japanese Patent Application No. 2016-180892, filed on Sep. 15, 2016.

TECHNICAL FIELD

The present invention relates to a sIgA-binding nucleic acid molecule, a sIgA analysis sensor, and a sIgA analysis method.

BACKGROUND ART

From the fact that stress can cause fatigue and depression, great importance is placed on stress check in recent years. However, there is a problem in that it is difficult to check whether a person is under stress by other persons owing to the fact that the person himself/herself may not be aware of the stress or that the stress is a subjective matter, for example. Under these circumstances, there is a demand for the establishment of a method for checking stress objectively.

It is known that, when humans feel stress, secretion of sIgA in saliva increases. On this account, there has been an attempt to evaluate stress indirectly by measuring sIgA in the saliva. Specifically, an ELISA method using an antibody against sIgA as an antigen has been reported (Non Patent Literature 1).

However, antibodies are proteins and thus have a problem in stability. Accordingly, it is difficult to use an antibody in a test method that can be carried out easily at low cost.

CITATION LIST

Non Patent Literature

Non Patent Literature 1: Isowa Keiko, "Relationship between Stressor in Duties of Nurses, Burnouts, and Physical Health Issues: Examination from Questionnaires and Immune Indicators", Behavioral Medicine Research, Vol. 10, No. 1, pp. 25-33

SUMMARY OF INVENTION

Technical Problem

With the foregoing in mind, the present invention is intended to provide a novel molecule that can be used for detection of sIgA.

Solution to Problem

The present invention provides a secretory immunoglobulin A (sIgA)-binding nucleic acid molecule that binds to sIgA with a dissociation constant of 37.7 nM or less.

The present invention also provides a sIgA analysis sensor including the sIgA-binding nucleic acid molecule of the present invention.

The present invention also provides a sIgA analysis method including the step of causing a specimen and a nucleic acid molecule to come into contact with each other to detect a sIgA in the specimen, wherein the nucleic acid molecule is the sIgA-binding nucleic acid molecule of the present invention, and in the detection step, the nucleic acid molecule is caused to bind to the sIgA in the specimen, and the sIgA in the specimen is detected by detecting the binding.

Advantageous Effects of Invention

The sIgA-binding nucleic acid molecule of the present invention can bind to sIgA with the above-described dissociation constant. Thus, the sIgA-binding nucleic acid molecule of the present invention can detect sIgA in a specimen with high accuracy on the basis of the presence or absence of the binding with the sIgA, for example. Therefore, it can be said that the sIgA-binding nucleic acid molecule of the present invention is a very useful tool for the detection of sIgA in the fields of preventive medicine, health care, diagnoses of infectious diseases, diagnoses of stress, and the like, for example.

DESCRIPTION OF EMBODIMENTS

Figure 1A:
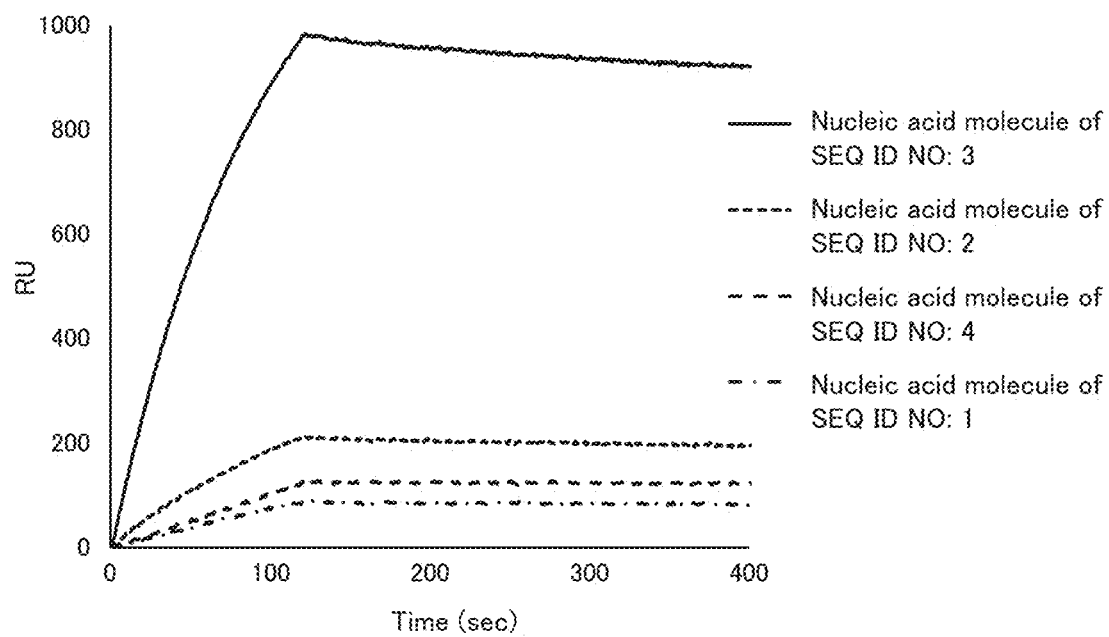
FIG. 1A is a graph showing the binding ability of aptamers to sIgA in Example 3.
Figure 1B:
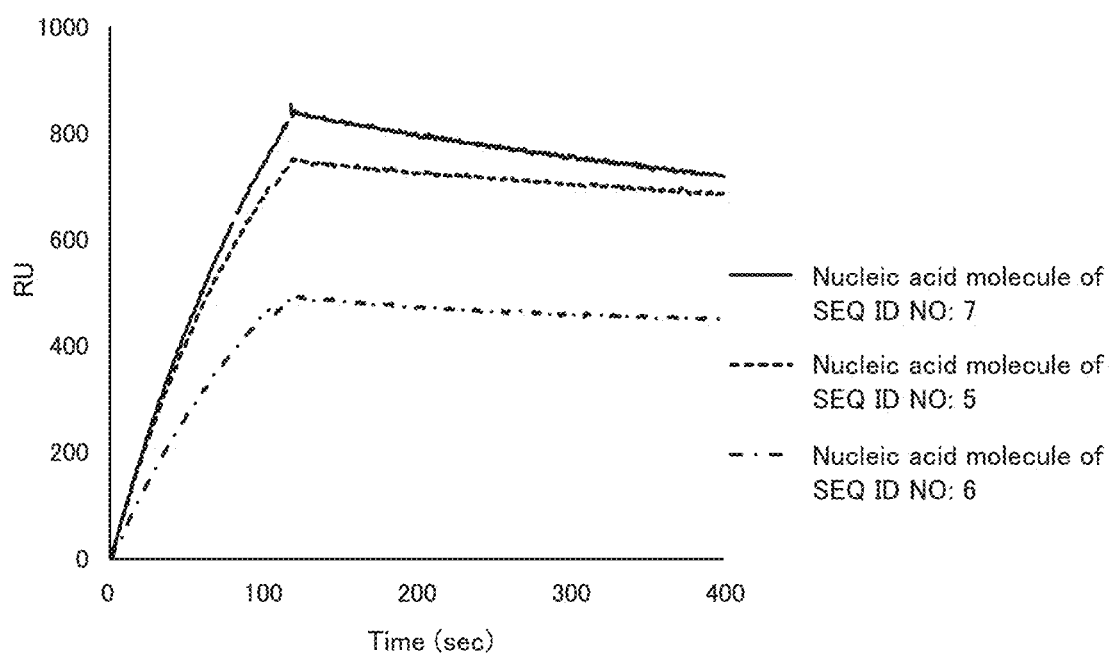
FIG. 1B is a graph showing the binding ability of other aptamers to sIgA in Example 3.
Figure 1C:
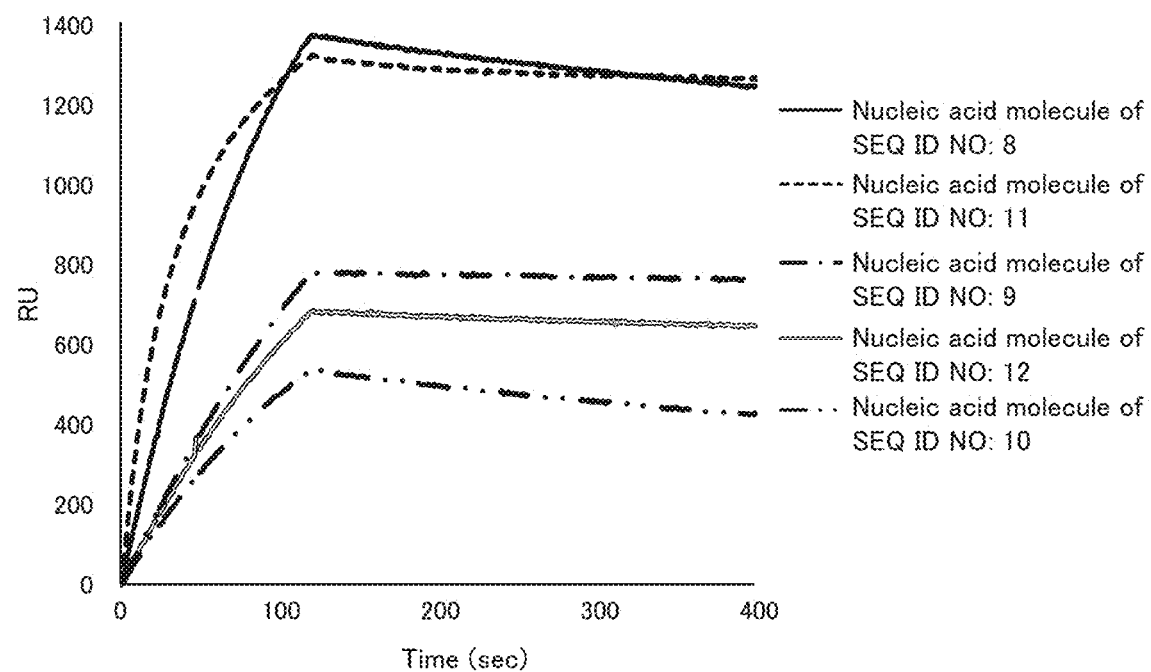
FIG. 1C is a graph showing the binding ability of other aptamers to sIgA in Example 3.
Figure 1D:
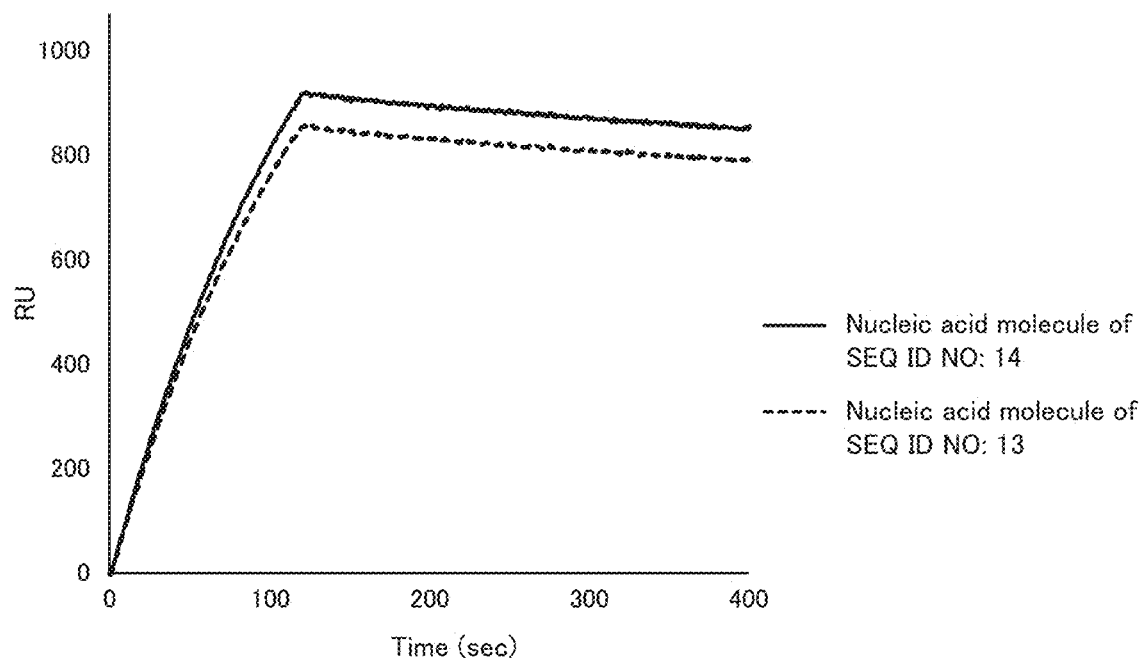
FIG. 1D is a graph showing the binding ability of other aptamers to sIgA in Example 3.
Figure 1E:
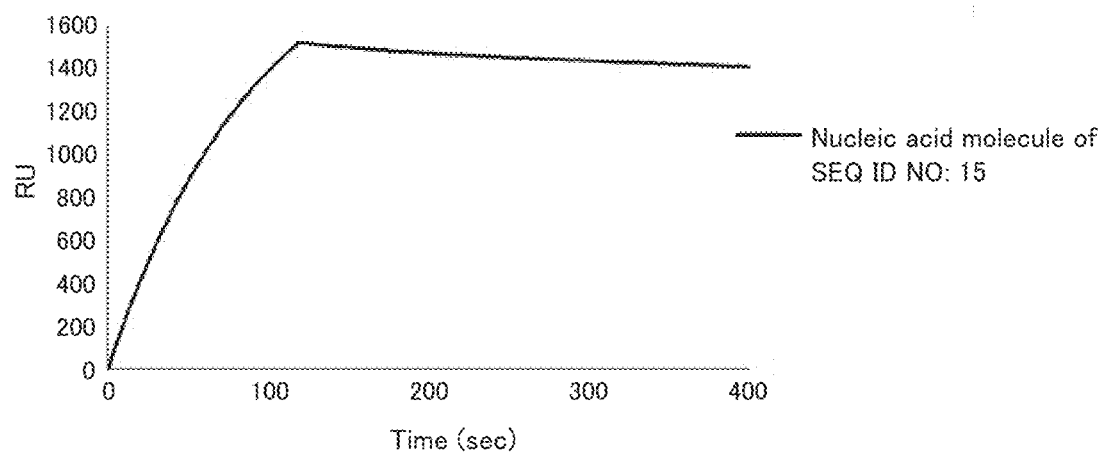
FIG. 1E is a graph showing the binding ability of another aptamer to sIgA in Example 3.
Figure 1F:
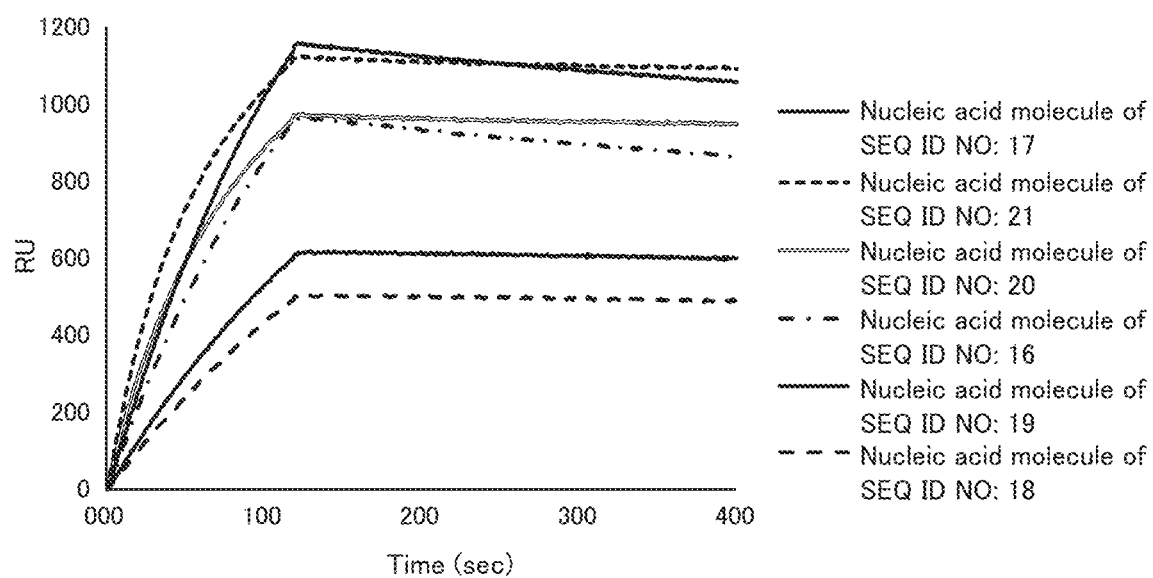
FIG. 1F is a graph showing the binding ability of other aptamers to sIgA in Example 3.
Figure 2A:
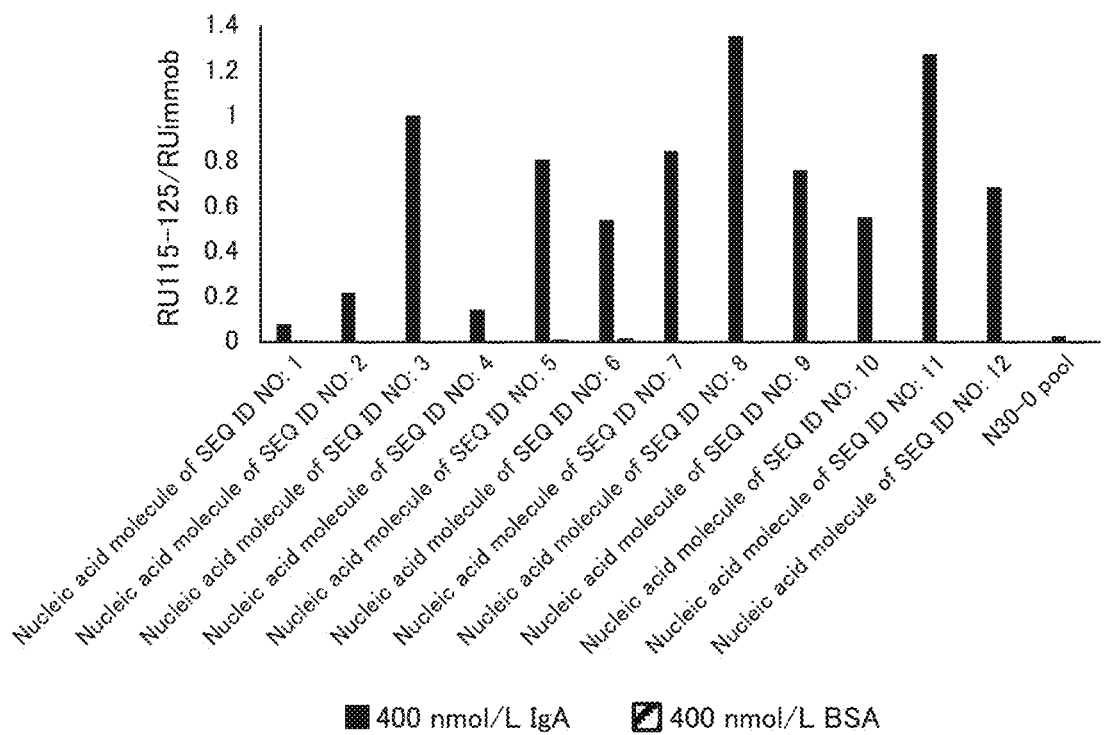
FIG. 2A is a graph showing the relative values (relative units) of the binding amounts of aptamers of Example 3 to sIgA.
Figure 2B:
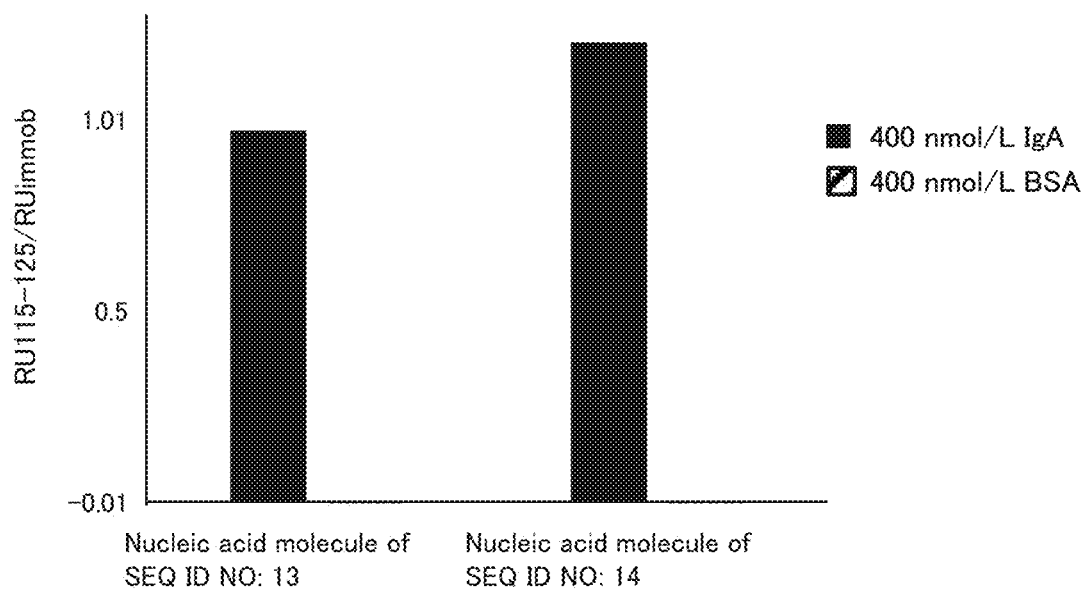
FIG. 2B is a graph showing the relative values (relative units) of the binding amounts of other aptamers of Example 3 to sIgA.
Figure 2C:
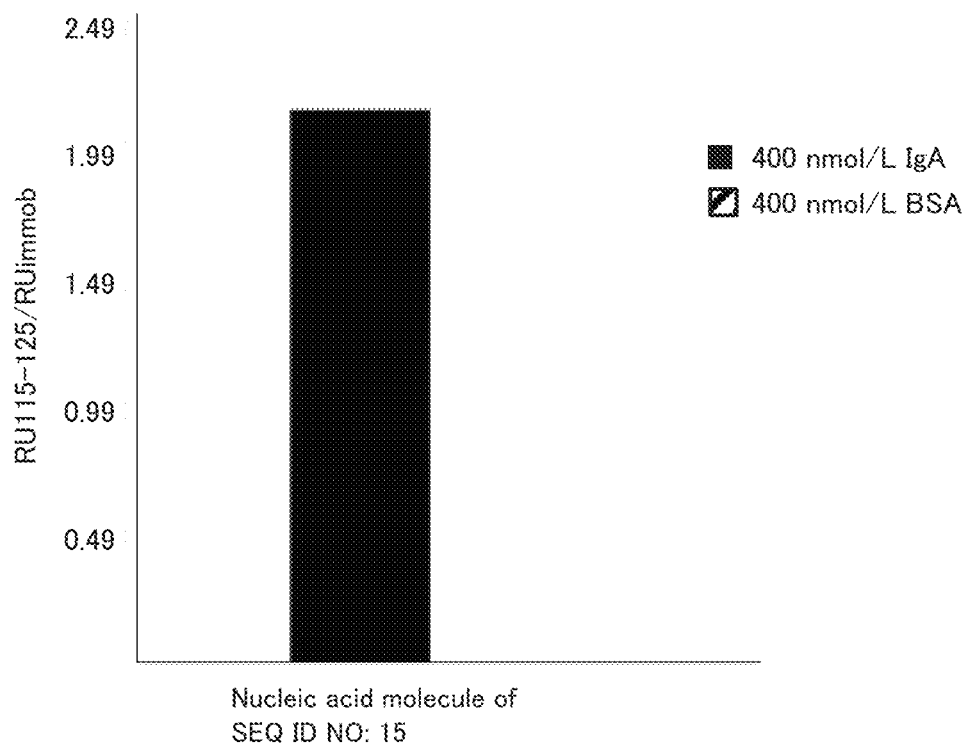
FIG. 2C is a graph showing the relative value (relative unit) of the binding amount of another aptamer of Example 3 to sIgA.
Figure 2D:
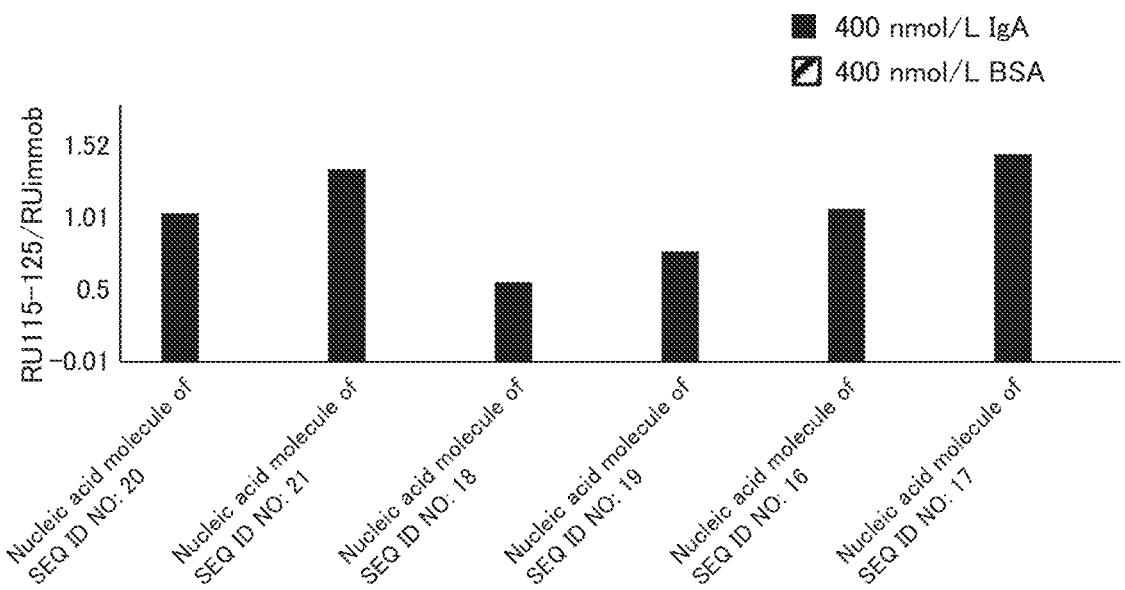
FIG. 2D is a graph showing the relative values (relative units) of the binding amounts of other aptamers of Example 3 to sIgA.

The sIgA-binding nucleic acid molecule of the present invention includes, for example, the following polynucleotide (a) or a polynucleotide consisting of a partial sequence thereof:

(a) a polynucleotide consisting of any of base sequences of SEQ ID NOs: 1 to 12.

In the sIgA-binding nucleic acid molecule of the present invention, the polynucleotide consisting of the partial sequence is, for example, at least one polynucleotide selected from the group consisting of the following polynucleotides (a1), (a2), (a3), and (a4):
(a1) a polynucleotide consisting of any of base sequences of SEQ ID NOs: 13, 14, and 15;
(a2) a polynucleotide consisting of either of base sequences of SEQ ID NOs: 16 and 17;
(a3) a polynucleotide consisting of either of base sequences of SEQ ID NOs: 18 and 19; and
(a4) a polynucleotide consisting of either of base sequences of SEQ ID NOs: 20 and 21.

The sIgA-binding nucleic acid molecule of the present invention may include, for example, a modified base, which is a base modified with a modifying group.

In the sIgA-binding nucleic acid molecule of the present invention, the modified base is, for example, a modified purine base, which is a purine base modified with a modifying group. The modifying group is preferably an adenine residue.

In the sIgA-binding nucleic acid molecule of the present invention, the modified base is a modified thymine, which is a thymine base modified with a modifying group, for example. The modifying group is preferably an adenine residue or a guanine residue.

In the sIgA-binding nucleic acid molecule of the present invention, the polynucleotide may be a DNA, for example.

In the sIgA analysis method of the present invention, the specimen may be at least one selected from the group consisting of saliva, urine, plasma, and serum, for example.

The present invention is described specifically below.

(1) sIgA-Binding Nucleic Acid Molecule

As described above, the sIgA-binding nucleic acid molecule (hereinafter also merely referred to as "nucleic acid molecule") of the present invention is characterized in that it binds to sIgA with a dissociation constant of 37.7 nM or less.

The nucleic acid molecule of the present invention can bind to sIgA, as mentioned above. The nucleic acid molecule of the present invention may bind to, for example, a heavy chain of immunoglobulin that constitutes sIgA, a light chain of the immunoglobulin, both of them, the bridges (J-strands) of two IgAs, or a secretory component that is bound to a sIgA. The sIgA is not particularly limited, and the sIgA may be derived from a human or a non-human animal, for example. Examples of the non-human animal include mice, rats, monkeys, rabbits, dogs, cats, horses, cows, and pigs. Amino acid sequence information on human Ig alpha-1 chain C region is registered under Accession No. P01876 in UniProt (http://www.uniprot.org/), for example. Amino acid sequence information on human Ig alpha-2 chain C region is registered under Accession No. P01877 in UniProt (http://www.uniprot.org/), for example.

In the present invention, the expression "binds to sIgA" (and grammatical variations thereof) also is referred to as "has binding ability to sIgA" or "has binding activity to sIgA", for example. The binding between the nucleic acid molecule of the present invention and the sIgA can be determined by surface plasmon resonance (SPR) analysis or the like, for example. The analysis can be performed using ProteON (trade name, BioRad), for example. Since the nucleic acid molecule of the present invention binds to sIgA, it can be used for detection of the sIgA, for example.

The nucleic acid molecule of the present invention binds to sIgA with a dissociation constant of 37.7 nM or less, 10 nM or less, 8 nM or less, or 5 nM or less, for example. The minimum detectable concentration of the sIgA by the nucleic acid molecule of the present invention is 50 nM, 20 nM, or 10 nM, for example.

The nucleic acid molecule of the present invention may be, for example, a nucleic acid molecule including the following polynucleotide (a), examples of which are shown in Table 1 below.

(a) a polynucleotide consisting of any of base sequences of SEQ ID NOs: 1 to 12.

TABLE 1

| SEQ ID NO: | Modified base | Base sequence |
|---|---|---|
| 1 | MK4 | 5'-GGTTTGGACGCAATCTCCCTAATCTACTACGATATCCAGATGGGAAGTGACCGTGAAACTACAATGGGCGGGCTTATC-3' |
| 2 | MK4 | 5'-GGTTTGGACGCAATCTCCCTAATCAGATGATATCGAGATGCGAAGCGACCGCATGAAACTACAATGGGCGGGCTTATC-3' |
| 3 | MK4 | 5'-GGTTTGGACGCAATCTCCCTAATCAAGCCACGGAGAGTCCGAGGTGACCATTAAGCAGGAAACTACAATGGGCGGGCTTA-3' |
| 4 | MK4 | 5'-GGTTTGGACGCAATCTCCCTAATCGATCTAGATGGTCTCGGGTATGGCTAGATAGAAACTACAATGGGCGGGCTTATC-3' |
| 5 | NG7 | 5'-GGTTTGGACGCAATCTCCCTAATCTGCTGATGTTTGTATTTCAAATTAGCCGCAGAAACTACAATGGGCGGGCTTATC-3' |
| 6 | NG7 | 5'-GGTTTGGACGCAATCTCCCTAATCTAAATAGATTTCACAGTGGATCCTTCAGAGGAAACTACAATGGGCGGGCTTATC-3' |
| 7 | NG7 | 5'-GGTTTGGACGCAATCTCCCTAATCAGACAATATTAGAGTGTTACCACCTGTGATGAAACTACAATGGGCGGGCTTATC-3' |
| 8 | KS9 | 5'-GGTTTGGACGCAATCTCCCTAATCGTATATCAAGCAGATGTGTTCACTTGGGGAGAAACTACAATGGGCGGGCTTATC-3' |
| 9 | KS9 | 5'-GGTTTGGACGCAATCTCCCTAATCAAAGATATGCTAAGATAGATAGTTTGGCTTGAAACTACAATGGGCGGGCTTATC-3' |
| 10 | KS9 | 5'-GGTTTGGACGCAATCTCCCTAATCACCTGTACTGGTTATTATGCCTGCCAACATGAAACTACAATGGGCGGGCTTATC-3' |
| 11 | KS9 | 5'-GGTTTGGACGCAATCTCCCTAATCTTTATACGTATGGACTTAGGCTTTGTTATAGAAACTACAATGGGCGGGCTTATC-3' |
| 12 | KS9 | 5'-GGTTTGGACGCAATCTCCCTAATCCTATCTGTTTTATCAATTGTAGCAAGTTATGAAACTACAATGGGCGGGCTTATC-3' |

The nucleic acid molecule of the present invention may be, for example, a nucleic acid molecule including a polynucleotide consisting of a partial sequence of any of the polynucleotides (a).

The polynucleotide consisting of the partial sequence may be, for example, at least one polynucleotide selected from the group consisting of the following polynucleotides (a1), (a2), (a3), and (a4).

(a1) a polynucleotide consisting of any of base sequences of SEQ ID NOs: 13, 14, and 15;
(a2) a polynucleotide consisting of either of base sequences of SEQ ID NOs: 16 and 17;
(a3) a polynucleotide consisting of either of base sequences of SEQ ID NOs: 18 and 19; and
(a4) a polynucleotide consisting of either of base sequences of SEQ ID NOs: 20 and 21.

The polynucleotide (a1) defines examples of a partial sequence of SEQ ID NO: 5. The polynucleotide (a2) defines examples of a partial sequence of SEQ ID NO: 8. The polynucleotide (a3) defines examples of a partial sequence of SEQ ID NO: 11. The polynucleotide (a4) defines examples of a partial sequence of SEQ ID NO: 12. These sequences are shown in Table 2 below.

TABLE 2

| SEQ ID NO: | Modified base | Base sequence |
| --- | --- | --- |
| 13 | NG7 | 5'-GGTTTGGACGCAATCTCCCTAATCTGCTGATGTTTGTATTTCAAATTAGCCGCAG-3' |
| 14 | NG7 | 5'-GCAATCTCCCTAATCTGCTGATGTTTGTATTTCAAATTAGCCGCAG-3' |
| 15 | NG7 | 5'-GCAATCTCCCTAATCTGCTGATGTTTGTATTTCAAATTAGC-3' |
| 16 | KS9 | 5'-GGTTTGGACGCAATCTCCCTAATCGTATATCAAGCAGATGTGTTCACTTGGGGAG-3' |
| 17 | KS9 | 5'-GCAATCTCCCTAATCGTATATCAAGCAGATGTGTTCACTTGGGGAG-3' |
| 18 | KS9 | 5'-GGTTTGGACGCAATCTCCCTAATCAAAGATATGCTAAGATAGATAGTTTGGCTTG-3' |
| 19 | KS9 | 5'-GCAATCTCCCTAATCAAAGATATGCTAAGATAGATAGTTTGGCTTG-3' |
| 20 | KS9 | 5'-GGTTTGGACGCAATCTCCCTAATCTTTATACGTATGGACTTAGGCTTTGTTATAGAAAC-3' |
| 21 | KS9 | 5'-GCAATCTCCCTAATCTTTATACGTATGGACTTAGGCTTTGTTATAGAAAC-3' |

In the binding nucleic acid molecule of the present invention, the polynucleotide encompasses, for example, at least one polynucleotide selected from the group consisting of the following polynucleotides (b) to (d):
(b) a polynucleotide that consists of a base sequence obtained by deletion, substitution, insertion, and/or addition of one or more bases in any of the base sequences of the polynucleotide (a) and binds to the sIgA;
(c) a polynucleotide that consists of a base sequence having at least 80% sequence identity to any of the base sequences of the polynucleotide (a) and binds to the sIgA; and
(d) a polynucleotide that consists of a base sequence complementary to a polynucleotide hybridizing to any of the base sequences of the polynucleotide (a) under stringent conditions and binds to the sIgA.

Regarding the polynucleotide (b), the term "one or more" is not limited as long as, for example, it is in the range where the polynucleotide (b) binds to sIgA. The number of the "one or more" bases is, for example, 1 to 10, 1 to 7, 1 to 5, 1 to 3, or 1 or 2. In the present invention, the numerical range regarding the number of bases, sequences, or the like discloses, for example, all the positive integers falling within that range. That is, for example, the description "1 to 5 bases" discloses all of "1, 2, 3, 4, and 5 bases" (the same applies hereinafter).

Regarding the polynucleotide (c), the "sequence identity" is not limited as long as, for example, it is in the range where the polynucleotide (c) binds to sIgA. The sequence identity is, for example, at least 80%, at least 85%, at least 90%, at least 95%, at least 96%, at least 97%, at least 98%, or at least 99%. The sequence identity can be calculated with analysis software such as BLAST or FASTA using default parameters, for example (the same applies hereinafter).

Regarding the polynucleotide (d), the "polynucleotide hybridizing to" may be, for example, a polynucleotide that is perfectly or partially complementary to the polynucleotide (a) and binds to the sIgA. The hybridization can be detected by various types of hybridization assay, for example. The hybridization assay is not particularly limited, and for example, a method described in "Molecular Cloning: A Laboratory Manual 2nd Ed." edited by Sambrook et al. (Cold Spring Harbor Laboratory Press (1989)) or the like can be employed.

Regarding the polynucleotide (d), the "stringent conditions" may be any of low stringency conditions, medium stringency conditions, and high stringency conditions, for example. The "low stringency conditions" are, for example, conditions where 5×SSC, 5×Denhardt's solution, 0.5% SDS, and 50% formamide are used at 32° C. The "medium stringency conditions" are, for example, conditions where 5×SSC, 5×Denhardt's solution, 0.5% SDS, and 50% formamide are used at 42° C. The "high stringency conditions" are, for example, conditions where 5×SSC, 5×Denhardt's solution, 0.5% SDS, and 50% formamide, are used at 50° C. Those skilled in the art can set the degree of stringency by, for example, setting the conditions such as the temperature, the salt concentration, the concentration and length of a probe, the ionic strength, the time, etc. as appropriate. As the "stringent conditions", it is also possible to employ conditions described in the above-described "Molecular Cloning: A Laboratory Manual 2nd Ed." edited by Sambrook et al. (Cold Spring Harbor Laboratory Press (1989)) or the like, for example.

The polynucleotides (a1) to (a4) are each a partial sequence of the polynucleotide (a). Thus, it can be said that they each define examples of the polynucleotide (b), (c), or (d), for example. When the nucleic acid molecule of the present invention is consisting of polynucleotides of (a1) to (a4), base sequences of the polynucleotide (a) in the polynucleotides (b) to (d) are the respective base sequences of the polynucleotides (a1) to (a4). In the description of the polynucleotides (b) to (d), "any of the base sequences of the polynucleotide (a)" and "polynucleotide (a)" can be read as "any of the base sequences of the polynucleotide (a1)" and "any of the polynucleotides (a1)", "any of the base sequences of the polynucleotide (a2)" and "any of the polynucleotides (a2)", "any of the base sequences of the polynucleotide (a3)" and "any of the polynucleotides (a3)", or "any of the base sequences of the polynucleotide (a4)" and "any of the polynucleotides (a4)", and the description of these can be incorporated in the description of "any of the base sequences of the polynucleotide (a)" and "polynucleotide (a)" by reference.

In the nucleic acid molecule of the present invention, the building blocks of the polynucleotide are, for example, nucleotide residues, examples of which include deoxyribonucleotide residues and ribonucleotide residues. The polynucleotide is, for example, a DNA consisting of deoxyribonucleotide residues or a DNA including a deoxyribonucleotide residue(s) and a ribonucleotide residue(s), and the polynucleotide may further include a non-nucleotide residue(s), as mentioned below. Hereinafter, the sIgA-binding nucleic acid molecule of the present invention is also referred to as an aptamer, for example.

The nucleic acid molecule of the present invention may consist of any of the above-described polynucleotides, or may include any of the above-described polynucleotides, for example. In the latter case, the nucleic acid molecule of the present invention may include, for example, two or more polynucleotides selected from the above-described polynucleotides, as mentioned below. The two or more polynucleotides may be the polynucleotides with the same sequence or different sequences. Also, in the latter case, the nucleic acid molecule of the present invention further may include a linker(s) and/or an additional sequence(s), for example. The linker is a sequence present between polynucleotides, for example. The additional sequence is a sequence added to an end, for example.

When the nucleic acid molecule of the present invention includes, for example, a plurality of polynucleotides selected from the above-described polynucleotides, it is preferable that the plurality of polynucleotide sequences are linked to each other to form a single-stranded polynucleotide. The plurality of polynucleotide sequences may be linked to each other directly, or may be linked to each other indirectly with a linker, for example. It is preferable that the polynucleotide sequences are linked to each other directly or indirectly at their ends. When the nucleic acid molecule of the present invention includes the plurality of polynucleotide sequences, the number of the sequences is not particularly limited, and is, for example, 2 or more, 2 to 20, 2 to 10, or 2 or 3.

The length of the linker is not particularly limited, and is, for example, 1- to 200-mer, 1- to 20-mer, 3- to 12-mer, or 5- to 9-mer. The building blocks of the linker are, for example, nucleotide residues, examples of which include deoxyribonucleotide residues and ribonucleotide residues. The linker is not particularly limited, and examples thereof include polynucleotides such as a DNA consisting of deoxyribonucleotide residues and a DNA including a ribonucleotide residue(s). Specific examples of the linker include polydeoxythymine (poly[dT]), polydeoxyadenine (poly[dA]), and poly(dA-dT) having a repetitive sequence composed of A and T. Preferably, the linker is poly(dT) or poly(dA-dT).

In the nucleic acid molecule of the present invention, the polynucleotide preferably is a single-stranded polynucleotide. It is preferable that the single-stranded polynucleotide can form a stem structure and a loop structure by self-annealing, for example. It is preferable that the polynucleotide can form a stem-loop structure, an internal loop structure, and/or a bulge structure, for example.

The nucleic acid molecule of the present invention may be a double strand, for example. When the nucleic acid molecule is a double strand, for example, one of single-stranded polynucleotides includes the polynucleotide (a), a partial sequence thereof, or any of the polynucleotides (b) to (d), and the other single-stranded polynucleotide is not limited. The other single-stranded polynucleotide may be, for example, a polynucleotide including a base sequence complementary to any of the polynucleotides (a) to (d). When the nucleic acid molecule of the present invention is a double strand, it is preferable to dissociate the double strand to single-stranded polynucleotides by denaturation or the like before use, for example. Also, it is preferable that the dissociated single-stranded polynucleotide including any of the polynucleotides (a) to (d) is forming a stem structure and a loop structure as mentioned above, for example.

In the present invention, the expression "can form a stem structure and a loop structure" encompasses that, for example, a stem structure and a loop structure are formed actually, and also, even if a stem structure and a loop structure are not formed, they can be formed depending on conditions. The expression "can form a stem structure and a loop structure (and grammatical variations thereof)" encompasses, for example, both the cases where the formation thereof has been confirmed through an experiment and where the formation thereof is predicted through simulation using a computer or the like.

The building blocks of the nucleic acid molecule of the present invention are, for example, nucleotide residues. Examples of the nucleotide residues include deoxyribonucleotide residues and ribonucleotide residues. The nucleic acid molecule of the present invention may be, for example, a DNA consisting of deoxyribonucleotide residues only or a DNA including one or more ribonucleotide residues. In the latter case, "one or more" is not particularly limited. For example, the number of the ribonucleotide residues in the polynucleotide is, for example, 1 to 91, 1 to 30, 1 to 15, 1 to 7, 1 to 3, or 1 or 2.

The polynucleotide may include, as a base in a nucleotide residue, a natural base or a modified base. The natural base (non-artificial base) is not particularly limited, and may be, for example, a purine base with a purine skeleton or a pyrimidine base with a pyrimidine skeleton. The purine base is not particularly limited, and examples thereof include adenine (a) and guanine (g). The pyrimidine base is not particularly limited, and examples thereof include cytosine (c), thymine (t), and uracil (u). Among them, cytosine (c) and thymine (t) are preferable.

When the polynucleotide includes the modified base(s), the site and the number of the modified bases are not particularly limited. When the partial sequence of the polynucleotide (a) has the modified base(s), some or all of the underlined adenines and thymines in the polynucleotides of Tables 1 and 2 are modified bases, for example. When the underlined adenine is the modified base, the modified base is a modified purine base, which is a purine base modified with a modifying group. When the underlined thymine is the modified base, the modified base is a modified thymine, which is a thymine base modified with a modifying group.

The modified base is a base modified with a modifying group, for example. The base to be modified with the modifying group (also referred to simply as the "base to be modified" hereinafter) is the natural base, for example. The natural base is not particularly limited, and may be, for example, a purine base or a pyrimidine base. The modified base is not particularly limited, and may be, for example, a modified adenine, a modified guanine, a modified cytosine, a modified thymine, or a modified uracil.

In the modified base, the base to be modified may be modified with the modifying group either directly or indirectly, for example. In the latter case, the base to be modified may be modified with the modifying group via a linker, for example. The linker is not particularly limited.

In the base to be modified, a site to be modified with the modifying group is not particularly limited. When the base is a purine base, the modified site in the purine base may be, for example, the 7-position or the 8-position, preferably the 7-position of the purine skeleton. When the modified site in the purine base is the 7-position of the purine skeleton, the nitrogen atom at the 7-position is preferably substituted with a carbon atom. When the base is a pyrimidine base, the modified site in the pyrimidine base may be, for example, the 5-position or the 6-position, preferably the 5-position of the pyrimidine skeleton. Thymine has a methyl group bound to carbon at the 5-position. Thus, when the 5-position of the pyrimidine base is modified, for example, the modifying group may be bound to the carbon at the 5-position either directly or indirectly, or the modifying group may be bound to carbon in the methyl group bound to the carbon at the 5-position either directly or indirectly. When the pyrimidine skeleton has "=O" bound to carbon at the 4-position and a group that is not "—CH$_3$" or "—H" bound to carbon at the 5-position, the modified base can be referred to as a modified uracil or a modified thymine.

When the modified base is a modified purine base, the modifying group is preferably an adenine residue. That is, the modified purine base is a base modified with an adenine residue, for example. In the base to be modified, a site to be modified with the adenine residue (binding site of the adenine residue to the base to be modified) is not particularly limited, and can be, for example, an amino group that binds to carbon at the 6-position of the adenine residue. The base to be modified with the adenine residue is not particularly limited, and preferably is a purine base, for example, and it is preferable that atom at the 7-position of the purine base is modified with the adenine residue. When the modified base is a modified thymine base, the modifying group is preferably an adenine residue or a guanine base. That is, the modified base is, for example, a base modified with an adenine residue or a guanine residue. In the base to be modified, a site to be modified with the adenine residue is not particularly limited, and can be, for example, an amino group that binds to carbon at the 6-position of the adenine residue. In the base to be modified, a site to be modified with the guanine residue is not particularly limited, and can be, for example, an amino group that binds to carbon at the 2-position of the guanine residue. The base to be modified with the adenine residue or the guanine residue is not particularly limited, and preferably is a thymine, for example, and it is preferable that carbon in a methyl group bound to the carbon at the 5-position of the thymine is modified with the adenine residue or the guanine residue.

When the modifying group is the adenine residue or the guanine residue, it is preferable that, for example, the base to be modified is modified with the modifying group via the linker, as shown below.

[nucleotide residue]-[linker]-[adenine residue]

[nucleotide residue]-[linker]-[guanine residue]

The linker is not particularly limited, and can be represented by, for example, each formula present between the nucleotide residue and the adenine residue/guanine residue, as shown below. It is to be noted, however, that the linker is not limited thereto. In each formula, the numerical value "n" in (CH$_2$)n is 1 to 10, 2 to 10, or 2, for example.

[nucleotide residue]=C—C(=O)—NH—(CH$_2$)$_n$-[adenine residue]

[nucleotide residue]=C—C(=O)—NH—(CH$_2$)$_n$-[guanine residue]

[nucleotide residue]-C=C—C(=O)—NH—(CH$_2$)$_n$-[adenine residue]

[nucleotide residue]=C—C(=O)—NH—CH$_2$—CH$_2$-[adenine residue]

[nucleotide residue]=C—C(=O)—NH—CH$_2$—CH$_2$-[guanine residue]

[nucleotide residue]-C=C—C(=O)—NH—CH$_2$—CH$_2$-[adenine residue]

In each formula, one ends of the linker [=C] and [—C] form a double bond and a single bond with carbon of the base to be modified in the nucleotide residue, respectively, for example, and the other end of the linker [CH$_2$—] is bound to amine (—NH) in the adenine residue or the guanine residue, for example.

Specific examples of an adenosine (purine derivative where the nitrogen atom at the 7-position is substituted with a carbon atom) nucleotide residue modified with the adenine residue in the polynucleotide include a residue represented by the following chemical formula (1) (also referred to as "MK4" hereinafter). Specific examples of a thymidine nucleotide residue modified with the adenine residue in the polynucleotide include a residue represented by the following chemical formula (2) (also referred to as "K59" hereinafter). Specific examples of a thymidine nucleotide residue modified with the guanine residue in the polynucleotide include a residue represented by the following formula (3) (also referred to as "NG7" hereinafter). It is to be noted, however, that the present invention is not limited thereto.

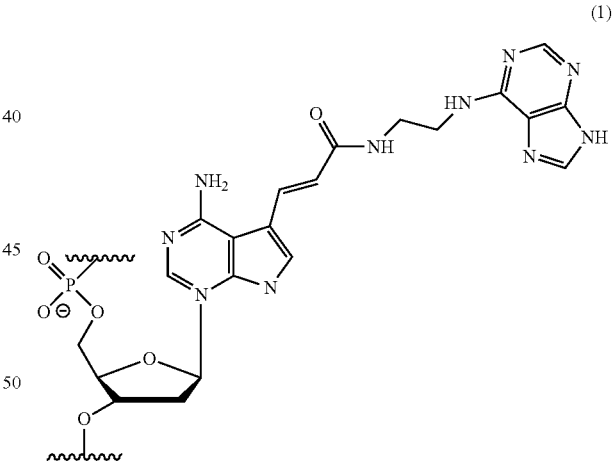

(1)

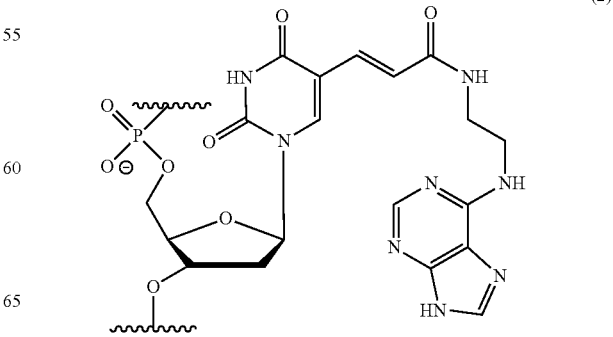

(2)

(3)

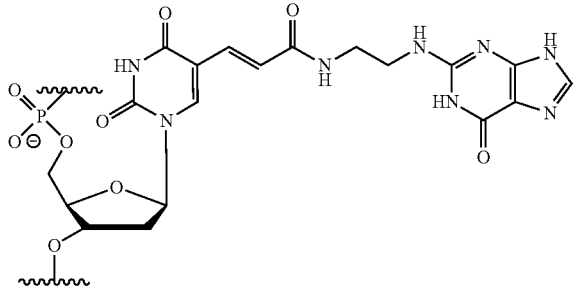

In the polynucleotides shown in Table 1 above, it is preferable that, for example, the underlined adenines are the nucleotide residues MK4. In the polynucleotides shown in Tables 1 and 2 above, it is preferable that, the underlined thymines are at least one of the nucleotide residues KS9 and NG7. In the polynucleotides shown in Tables 1 and 2 above, for example, it is preferable that the underlined thymines in the polynucleotides consisting of the respective base sequences of SEQ ID Nos: 5 to 7 and 13 to 15 are nucleotide residues NG7. In the polynucleotides shown in Tables 1 and 2 above, for example, it is preferable that the underlined thymines in the polynucleotides consisting of the respective base sequences of SEQ ID Nos: 8 to 12 and 16 to 21 are nucleotide residues KS9.

When the nucleic acid molecule of the present invention includes the adenosine nucleotide residues, the polynucleotide can be synthesized using, as a monomer molecule, a nucleotide triphosphate represented by the following chemical formula (4) (hereinafter also referred to as "MK4 monomer" hereinafter), for example. For example, when the nucleic acid molecule of the present invention includes the thymidine nucleotide residues, the polynucleotide can be synthesized using, as a monomer molecule, a nucleotide triphosphate represented by the following chemical formula (5) (also referred to as "KS9 monomer" hereinafter) or a nucleotide triphosphate represented by the following chemical formula (6) (also referred to as "NG7 monomer" hereinafter), for example. In the synthesis of the polynucleotide, for example, the monomer molecule binds to another nucleotide triphosphate via a phosphodiester bond. A method for producing the MK4 monomer and the NG7 monomer is described below.

(4)

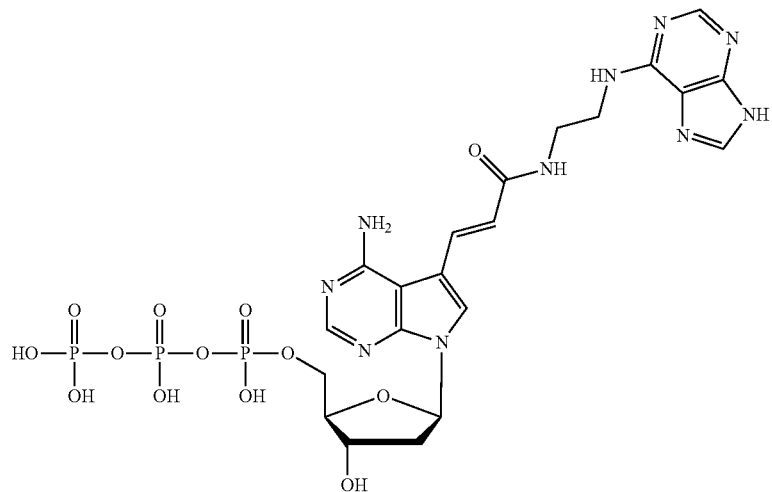

(5)

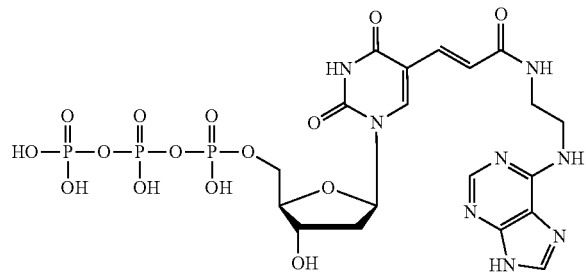

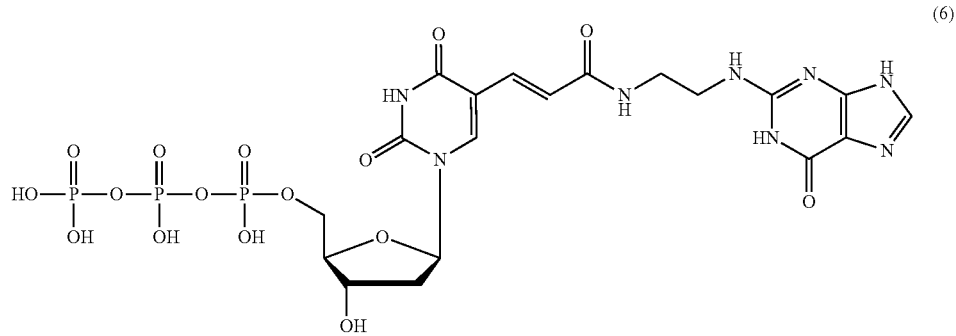

(6)

Other examples of the modifying group include methyl group, fluoro group, amino groups, thio group, a benzylaminocarbonyl group, a tryptaminocarbonyl group, and an isobutylaminocarbonyl group.

Specific examples of the modified adenine include 7'-deazaadenine. Specific examples of the modified guanine include 7'-deazaguanine. Specific examples of the modified cytosine include 5'-methylcytosine (5-Me-dC). Specific examples of the modified thymine include 5'-benzylaminocarbonyl thymine, 5'-tryptaminocarbonyl thymine, and 5'-isobutylaminocarbonyl thymine. Specific examples of the modified uracil include 5'-benzylaminocarbonyl uracil (BndU), 5'-tryptaminocarbonyl uracil (TrpdU), and 5'-isobutylaminocarbonyl uracil. The modified uracils given above as examples also can be referred to as modified thymines.

The polynucleotide may include only one type or two or more types of the modified bases, for example.

The nucleic acid molecule of the present invention may be a modified nucleotide, for example. The modified nucleotide may be a nucleotide having the above-described modified base, a nucleotide having a modified sugar obtained through modification of a sugar residue, or a nucleotide having the modified base and the modified sugar.

The sugar residue is not particularly limited, and may be a deoxyribose residue or a ribose residue, for example. The modified site in the sugar residue is not particularly limited, and may be, for example, the 2'-position or the 4'-position of the sugar residue. Either one or both of the 2'-position and the 4'-position may be modified. Examples of a modifying group in the modified sugar include methyl groups, fluoro groups, amino groups, and thio groups.

When the base in the modified nucleotide residue is a pyrimidine base, it is preferable that the 2'-position and/or the 4'-position of the sugar residue is modified, for example. Specific examples of the modified nucleotide residue include modified nucleotide residues with the 2'-position of the deoxyribose residue or ribose residue being modified, such as a 2'-methylated-uracil nucleotide residue, 2'-methylated-cytosine nucleotide residue, 2'-fluorinated-uracil nucleotide residue, 2'-fluorinated-cytosine nucleotide residue, 2'-aminated-uracil nucleotide residue, 2'-aminated-cytosine nucleotide residue, 2'-thiated-uracil nucleotide residue, and 2'-thiated-cytosine nucleotide residue.

The number of the modified nucleotides is not particularly limited. For example, the number of the modified nucleotides in the polynucleotide is, for example, 1 to 100, 1 to 90, 1 to 80, or 1 to 70. Also, the number of the modified nucleotides in the full-length nucleic acid molecule including the polynucleotide is not particularly limited, and is, for example, 1 to 91, 1 to 78, or in the numerical ranges given above as examples of the number of the modified nucleotides in the polynucleotide.

The nucleic acid molecule of the present invention may include, for example, one or more artificial nucleic acid monomer residues. The term "one or more" is not particularly limited, and may be, for example, 1 to 100, 1 to 50, 1 to 30, or 1 to 10 in the polynucleotide, for example. Examples of the artificial nucleic acid monomer residue include peptide nucleic acids (PNAs), locked nucleic acids (LNAs), and 2'-O,4'-C-ethylenebridged nucleic acids (ENAs). The nucleic acid in the monomer residue is the same as described above, for example.

It is preferable that the nucleic acid molecule of the present invention is resistant to nuclease, for example. In order to allow the nucleic acid molecule of the present invention to have nuclease resistance, it is preferable that the nucleic acid molecule of the present invention includes the modified nucleotide residue(s) and/or the artificial nucleic acid monomer residue(s), for example. Also, in order to allow the nucleic acid molecule of the present invention to have nuclease resistance, the nucleic acid molecule of the present invention may have polyethylene glycol (PEG) of several tens of kDa, deoxythymidine, or the like bound to, e.g., the 5' end or the 3' end thereof.

The nucleic acid molecule of the present invention may further include an additional sequence, for example. Preferably, the additional sequence is bound to at least one of the 5' end and the 3' end, more preferably to the 3' end of the nucleic acid molecule, for example. The additional sequence is not particularly limited. The length of the additional sequence is not particularly limited, and is, for example, 1- to 200-mer, 1- to 50-mer, 1- to 25-mer, or 18- to 24-mer. The building blocks of the additional sequence are, for example, nucleotide residues, examples of which include deoxyribonucleotide residues and ribonucleotide residues. The additional sequence is not particularly limited, and examples thereof include polynucleotides such as a DNA consisting of deoxyribonucleotide residues and a DNA including a ribonucleotide residue(s). Specific examples of the additional sequence include poly(dT) and poly(dA).

The nucleic acid molecule of the present invention can be used in the state where it is immobilized on a carrier, for example. It is preferable to immobilize either the 5' end or the 3' end, more preferably the 3' end of the nucleic acid molecule of the present invention, for example. When the nucleic acid molecule of the present invention is immobilized, the nucleic acid molecule may be immobilized either directly or indirectly on the carrier, for example. In the latter case, it is preferable to immobilize the nucleic acid molecule via the additional sequence, for example.

The method for producing the nucleic acid molecule of the present invention is not particularly limited. For example, the nucleic acid molecule of the present invention can be synthesized by known methods such as: nucleic acid synthesis methods utilizing chemical synthesis; and genetic engineering procedures. The nucleic acid molecule of the present invention also can be obtained by a so-called SELEX method, for example. In this case, a target preferably is sIgA.

The nucleic acid molecule of the present invention exhibits binding properties to the sIgA, as mentioned above. Thus, use of the nucleic acid molecule of the present invention is not particularly limited, as long as it is the use utilizing the binding properties of the nucleic acid molecule to the sIgA. The nucleic acid molecule of the present invention can be used in various methods as an alternative to, e.g., an antibody against the sIgA.

(2) sIgA Analysis Sensor

As described above, the analysis sensor of the present invention is a sIgA analysis sensor characterized in that it includes the nucleic acid molecule of the present invention. It is only required that the analysis sensor of the present invention includes the nucleic acid molecule of the present invention, and other configurations are not particularly limited. By using the analysis sensor of the present invention, the sIgA can be detected by, for example, causing the nucleic acid molecule to bind to the sIgA, as described above.

The analysis sensor of the present invention may be configured so that, for example, it further includes a carrier, and the nucleic acid molecule is disposed on the carrier. Preferably, the nucleic acid molecule is immobilized on the carrier. The immobilization of the nucleic acid molecule on the carrier is as described above, for example. The method for using the analysis sensor of the present invention is not particularly limited, and the descriptions of the nucleic acid molecule and the analysis method of the present invention can be incorporated in the description of the analysis sensor of the present invention by reference.

(3) Analysis Method

As mentioned above, the analysis method of the present invention is a method including the step of: causing a specimen and a nucleic acid molecule to come into contact with each other to detect a secretory immunoglobulin A (sIgA) in the specimen, wherein the nucleic acid molecule is the sIgA-binding nucleic acid molecule of the present invention, and in the detection step, the nucleic acid molecule is caused to bind to the sIgA in the specimen, and the sIgA in the specimen is detected by detecting the binding. The analysis method of the present invention is characterized in that it uses the nucleic acid molecule of the present invention, and other steps, conditions, etc. are not particularly limited. In the analysis method of the present invention, the sIgA analysis sensor of the present invention may be used as the nucleic acid molecule of the present invention.

The nucleic acid molecule of the present invention specifically binds to sIgA. Thus, of the present invention, it is possible to specifically detect sIgA in a specimen by detecting the binding between the sIgA and the nucleic acid molecule, for example. Specifically, since the present invention can analyze the presence or absence or the amount of sIgA in a specimen, for example, it can be said that the present invention also can perform qualitative or quantitative analysis of the sIgA.

In the present invention, the specimen is not particularly limited. Examples of the specimen include saliva, urine, plasma, and serum.

The specimen may be a liquid specimen or a solid specimen, for example. The specimen preferably is a liquid specimen from the viewpoint of ease of handling because the liquid specimen can be brought into contact with the nucleic acid molecule more easily, for example. In the case of the solid specimen, a liquid mixture, a liquid extract, a solution, or the like of the solid specimen prepared using a solvent may be used, for example. The solvent is not particularly limited, and may be water, physiological saline, or a buffer solution, for example.

The above-described detection step includes, for example: a contact step of causing the specimen and the nucleic acid molecule to come into contact with each other to cause the nucleic acid molecule to bind to the sIgA in the specimen; and a binding detection step of detecting the binding between the sIgA and the nucleic acid molecule. The detection step may further include, for example, an analysis step of analyzing the presence or absence or the amount of the sIgA in the specimen on the basis of the result obtained in the binding detection step.

In the contact step, the method for causing the specimen and the nucleic acid molecule to come into contact with each other is not particularly limited. The contact between the specimen and the nucleic acid molecule preferably is achieved in a liquid, for example. The liquid is not particularly limited, and may be, for example, water, physiological saline, or a buffer solution.

In the contact step, the conditions under which the contact between the specimen and the nucleic acid molecule is caused are not particularly limited. The contact temperature is, for example, 4° C. to 37° C., or 18° C. to 25° C., and the contact time is, for example, 10 to 120 minutes or 30 to 60 minutes.

In the contact step, the nucleic acid molecule may be an immobilized nucleic acid molecule immobilized on a carrier or an unimmobilized nucleic acid molecule in a free state, for example. In the latter case, the nucleic acid molecule is brought into contact with the specimen in a container, for example. The nucleic acid molecule preferably is the immobilized nucleic acid molecule from the viewpoint of favorable handleability, for example. The carrier is not particularly limited, and may be, for example, a substrate, beads, or a container. The container may be a microplate or a tube, for example. The immobilization of the nucleic acid molecule is as described above, for example.

The binding detection step is the step of detecting the binding between the sIgA in the specimen and the nucleic acid molecule, as described above. By detecting the presence or absence of the binding between the sIgA and the nucleic acid molecule, it is possible to analyze the presence or absence of the sIgA in the specimen (qualitative analysis), for example. Also, by detecting the degree of the binding (the binding amount) between the sIgA and the nucleic acid molecule, it is possible to analyze the amount of the sIgA in the specimen (quantitative analysis), for example.

In the case where the binding between the sIgA and the nucleic acid molecule cannot be detected, it can be determined that no sIgA is present in the specimen. In the case where the binding is detected, it can be determined that the sIgA is present in the specimen.

The method for analyzing the binding between the sIgA and the nucleic acid molecule is not particularly limited. A conventionally known method for detecting the binding between substances may be employed as the method, for example, and specific examples of the method include the above-described SPR. Detection of the binding may be detection of a complex of the sIgA and the nucleic acid molecule, for example.

(4) Detection Kit

A detection kit of the present invention is characterized in that it includes the sIgA-binding nucleic acid molecule of the present invention. It is only required that the detection kit of the present invention includes the nucleic acid molecule of the present invention, and other configurations are by no means limited. By using the detection kit of the present invention, it is possible to perform the detection and the like of the sIgA as mentioned above, for example.

The detection kit of the present invention may include the sensor of the present invention as the nucleic acid molecule of the present invention, for example. The detection kit of the present invention further may include any component(s) in addition to the nucleic acid molecule of the present invention, for example. Examples of the component include the above-described carrier, a buffer solution, and instructions for use.

EXAMPLES

Next, examples of the present invention are described below. It is to be noted, however, that the present invention is by no means limited by the following examples. Commercially available reagents in the examples were used in accordance with their protocols, unless otherwise stated.

Example 1

MK4 was prepared by the following synthesis examples.

Electrospray ionization mass spectrometry (ESI-MS) was performed using a mass spectrometer (API2000, vendor: Applied Biosystems) in positive or negative ion mode. $^1$H NMR spectra were obtained using a nuclear magnetic resonance instrument (JNM-ECS400, manufactured by JEOL). Chemical shifts are expressed as relative δ (ppm) to the internal standard, tetramethylsilane (Me$_4$Si). Ion-exchange chromatography was performed using a chromatographic system (ECONO system, manufactured by Bio-Rad). In the ion-exchange chromatography, a glass column (φ25×500 mm) packed with diethylaminoethyl (DEAE) A-25-Sephadex (manufactured by Amershambiosciences) was used.

(Synthesis Example 1) Synthesis of MK1

Scheme 1

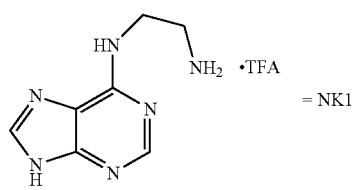

= NK1

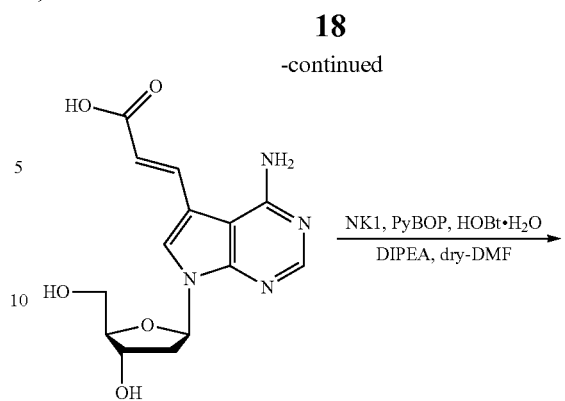

AZ6
Exact Mass: 320.11
Molecular Weight: 320.30

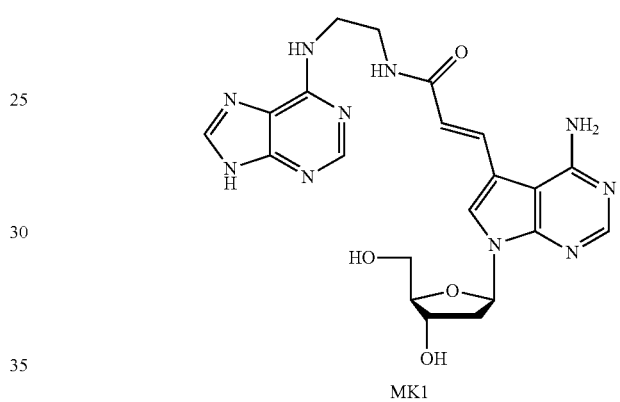

MK1
Exact Mass: 480.20
Molecular Weight: 480.49

AZ6 (290 mg, 9.06×10$^{-4}$ mol) was dried in vacuo and dissolved in dry-DMF (N,N-dimethylformamide, 3 mL). To this solution, HOBt.H$_2$O (1-hydroxybenzotriazole monohydrate, 176 mg, 1.15×10$^{-5}$ mol, 1.2 eq.), PyBOP® (hexafluorophosphoric acid (benzotriazole-1-yloxy)tripyrrolidinophosphonium, 579 mg, 1.15×10$^{-5}$ mol, 1.2 eq.), and DIPEA (N,N-diisopropylethylamine, 4.6 mL, 2.72×10$^{-2}$ mol, 30 eq.) were added, and NK1 (493 mg, 9.48×10$^{-4}$ mol, 1.1 eq.) dissolved in dry-DMF (1 mL) was further added and stirred. After 40 minutes from the initiation of the stirring, the solvent was distilled off under reduced pressure, and a residue was dissolved in water, and a precipitate was collected by suction filtration. The filtrate was roughly purified by reversed-phase column chromatography, to give MK1.

Physical properties of MK1 are shown below.

Yield amount: 261 mg, Yield: 60%

ESI-MS (positive ion mode) m/z, found=481.2, calculated for [(M+H)+]=481.2.

Found=503.1, calculated for [(M+Na)+]=503.2.

$^1$HNMR (400 MHz, DMSO-d6) δ8.22 (1H, m), 8.11 (1H, s), 8.10 (1H, s), 7.87 (1H, s), 7.63 (1H, d), 6.52 (1H, q), 6.35 (1H, d), 5.27 (1H, s), 3.82 (1H, m), 2.18 (1H, m)

(Synthesis Example 2) Synthesis of MK2

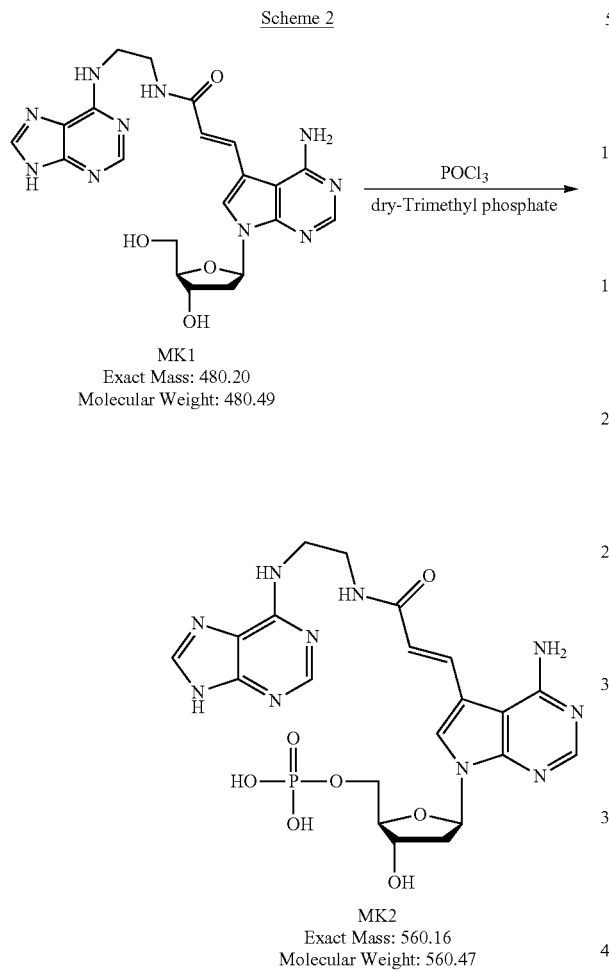

MK1 (108 mg, 2.25×10$^{-4}$ mol) was dried in vacuo, and the atmosphere was replaced with Argon (Ar). Subsequently, azeotropy between the MK1 and dry-DMF was caused twice (the first time: 40 mL, the second time: 4 mL), and azeotropy between the MK1 and dry-MeCN (acetonitrile) was caused three times (the first time: 9 mL, the second time: 5 mL, the third time: 5 mL). The resultant azeotrope was suspended in dry-Trimethyl phosphate (6 mL), and thereafter, dry-Tributhyl amine (130 µL, 5.44×10$^{-4}$ mol, 2.5 eq.) was added thereto. Then, phosphoryl chloride (42 µL, 4.50×10$^{-4}$ mol, 2 eq.) was added and stirred under ice cooling. After 40 minutes from the initiation of the stirring, dry-Tributhyl amine (250 µL, 1.05×10$^{-3}$ mol, 5 eq.) and Phosphoryl chloride (84 µL, 4.50×10$^{-4}$ mol, 4 eq.) were again added and stirred under ice cooling for 1 hour. After the stirring, a cooled 1 mol/L TEAB (Triethylammonium bicarbonate) buffer (5 mL) was added, stirred for 5 minutes, and quenched. Then, the solvent was distilled off under reduced pressure, crystallization was performed in Ether, and suction filtration was performed to obtain a yellow solid. The yellow solid was dissolved in water, purified by anion-exchange chromatography, and freeze-dried, to give MK2. Physical properties of MK2 are shown below.

Yield amount: 30.0 µmol, Yield: 13.4%
ESI-MS (negative ion mode) m/z, found=559.1, calculated for [(M−H)−]=559.2

(Synthesis Example 3) Synthesis of MK3

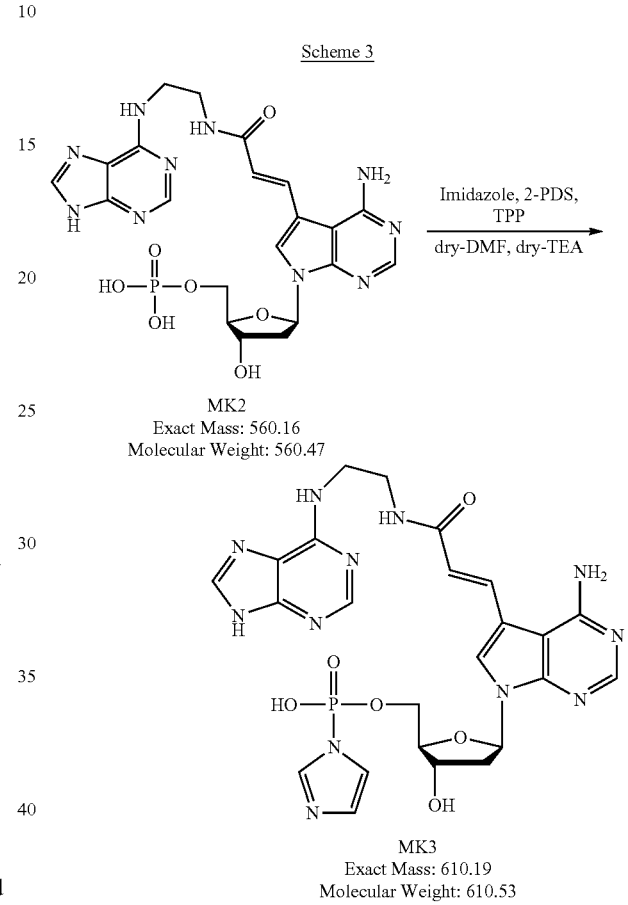

MK2 (30.03 µmol) was dried in vacuo, and azeotropy between the MK2 and dry-Pyridine (10 mL) was performed three times, and the azeotrope was dried in vacuo overnight. After the drying, the atmosphere was replaced with Ar, and the MK2 was dissolved in dry-DMF (2 mL) and dry-TEA (triethylamine, 28 µL, 1.98×10$^{-4}$ mol, 6.6 eq.). Further, Imidazole (16 mg, 14.02×10$^{-4}$ mol, 4 eq.), 2,2'-Dithiodipyridine (17 mg, 7.72×10$^{-4}$ mol, 1.6 eq.), and Triphenylphosphine (20 mg, 7.63×10$^{-4}$ mol, 1.6 eq.) were added and stirred at room temperature. After 6.5 hours from the initiation of the stirring, the resultant reaction solution was added to a solution of Sodium perchlorate (39 mg, 3.19×10$^{-4}$ mol, 10 eq.) in dry-Acetone (18 mL), dry Ether (27 mL), and dry-TEA (2 mL), and allowed to stand at 4° C. for 30 minutes. The precipitate was decanted 5 times with dry-Ether (12 mL) and was thereafter dried in vacuo, to give MK3 as a crude.

Theoretical yield amount: 30.03 µmol

(Synthesis Example 4) Synthesis of MK4

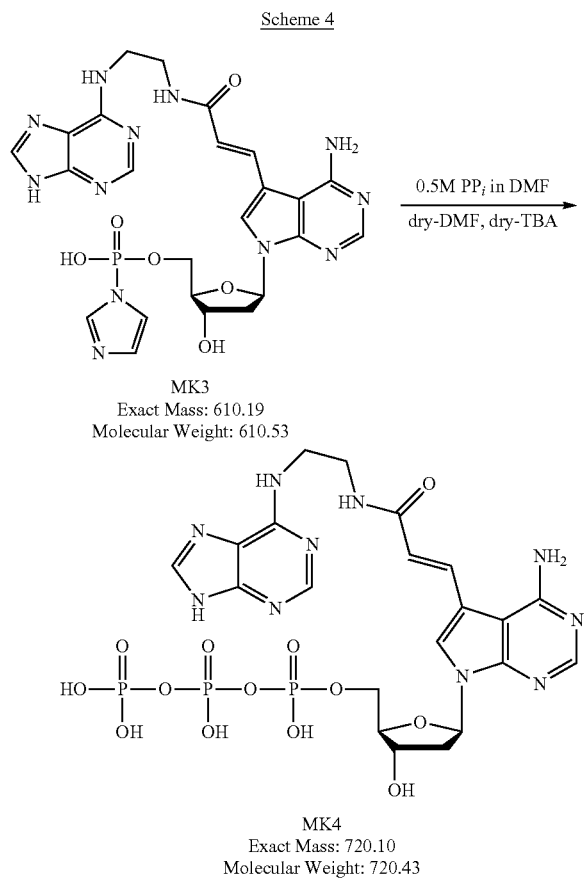

Scheme 4

MK3
Exact Mass: 610.19
Molecular Weight: 610.53

MK4
Exact Mass: 720.10
Molecular Weight: 720.43

MK3 (30.03 µmol) was dried in vacuo, the atmosphere was replaced with Ar, and then, azeotropy between the MK3 and dry-Pyridine (5 mL) was caused twice, and the azeotrope was then suspended in dry-DMF (1 mL). Further, dry-n-Tributylamine (30 µL, $1.25 \times 10^{-4}$ mol, 4 eq.) and 0.5 mol/L n-Tributylamine pyrophosphate in DMF (310 µL, $1.53 \times 10^{-4}$ mol, 5 eq.) were added to the suspension and then stirred at room temperature. After 6.5 hours from the initiation of the stirring, a 1 mol/L TEAB buffer (5 mL) was added and stirred for 30 minutes, and then the solvent was distilled off under reduced pressure. Water was added, an aqueous layer was separated with Ether twice, purified by anion-exchange column chromatography, and freeze-dried, to give MK4. Physical properties of MK4 are shown below.

Yield amount: 3.33 µmol, Yield: 11.1%

ESI-MS (negative ion mode) m/z, found=719.0, calculated for [(M−H)−]=719.1

Example 2

NG7 was prepared by the following synthesis example.

Electrospray ionization mass spectrometry (ESI-MS) was performed using a mass spectrometer (API2000, vendor: Applied Biosystems) in positive or negative ion mode. $^1$H NMR spectra were obtained using a nuclear magnetic resonance instrument (JNM-ECS400, manufactured by JEOL). Chemical shifts are expressed as relative δ (ppm) to the internal standard, tetramethylsilane (Me$_4$Si). Ion-exchange chromatography was performed using a chromatographic system (ECONO system, manufactured by Bio-Rad). In the ion-exchange chromatography, a glass column (φ25×500 mm) packed with diethylaminoethyl (DEAE) A-25-Sephadex (manufactured by Amershambiosciences) was used.

(Synthesis Example 1) Synthesis of NH1

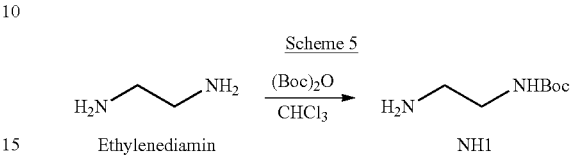

Scheme 5

Ethylenediamin      NH1

CHCl$_3$ (20 mL) containing tert-butyl dicarbonate (5 g, 22.9 mmol, 0.2 eq.) dissolved therein was added dropwise to CHCl$_3$ (120 mL) containing ethylendiamine (7 mL, 105 mmol, 1 eq.) dissolved therein while stirring. After 24 hours from the addition, the solution was subjected to suction filtration, and the solvent was distilled off under reduced pressure to give NH1. Physical properties of NH1 are shown below.

Yield amount: 3.573 g, Yield: 97.4%

ESI-MS (positive ion mode) m/z, found=161.4, calculated for [(M+H)+]=161.1

$^1$HNMR (400 MHz, CDCl$_3$) δ3.13 (2H, q) 2.76 (2H, t) 1.41 (9H, s)

(Synthesis Example 2) Synthesis of NG1

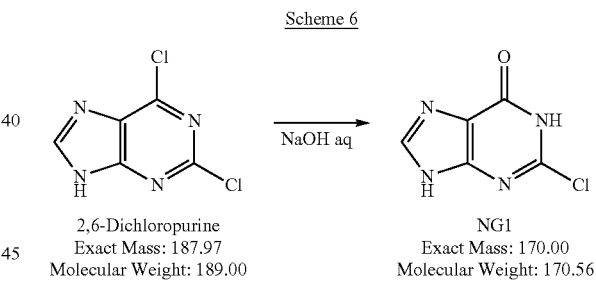

Scheme 6

2,6-Dichloropurine
Exact Mass: 187.97
Molecular Weight: 189.00

NG1
Exact Mass: 170.00
Molecular Weight: 170.56

The atmosphere of 2,6-Dichloropurine (1000 mg, $5.29 \times 10^{-3}$ mol, 10. eq.) was replaced with Ar (argon), and the 2,6-Dichloropurine was dissolved in an aqueous sodium hydroxide solution (10.6 mL, $2.12 \times 10^{-2}$ mol, 2N) and refluxed at 90° C., to cause a reaction. After the reaction, the temperature was returned to room temperature, and the solution was subjected to suction filtration. The obtained filtrate was collected, dissolved in a minimal amount of water, the pH was adjusted to 3 to 4, and the precipitated filtrate was collected by suction filtration to give NG1. The physical properties of NG1 are shown below.

Yield amount: 720 mg, Yield: 79%

ESI-MS (positive ion mode) m/z, found=171.0, calculated for [(M+H)+]=171.0.

found=193.1, calculated for [(M+Na)+]=193.0.

found=209.1, calculated for [(M+K)+]=209.0.

ESI-MS (negative ion mode) m/z, found=169.0, calculated for [(M−H)−]=518.0.

$^1$HNMR (400 MHz, DMSO-d6) δ8.29 (1H, s)

(Synthesis Example 3) Synthesis of NG2

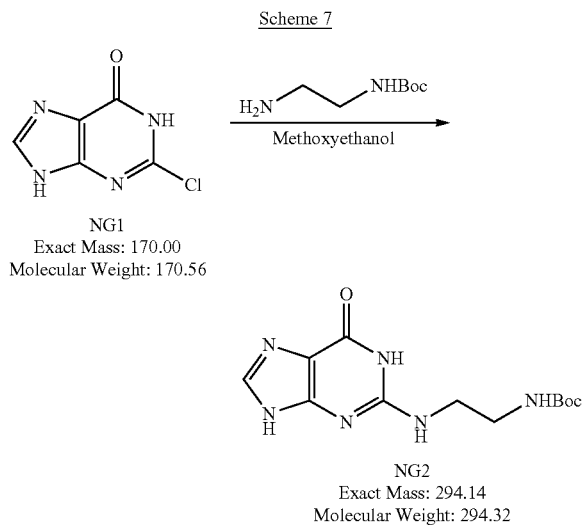

Scheme 7

NG1
Exact Mass: 170.00
Molecular Weight: 170.56

NG2
Exact Mass: 294.14
Molecular Weight: 294.32

Each of NG1 (870 mg, $5.10 \times 10^{-3}$ mol) and NH1 (3.281 g, $2.05 \times 10^{-2}$ mol, 4 eq.) was dried in vacuo, and the atmospheres of the NG1 and the NH1 were replaced with Ar. The NG1 was suspended in Methoxyethanol (5 mL), and the NH1 was dissolved in Methoxyethanol (1 mL). The obtained NH1 solution was transferred to a recovery flask containing the NG1, which was then refluxed at 130° C., to cause a reaction. After the reaction, the temperature was returned to room temperature, and the solvent in the solution was distilled off under reduced pressure. The solution was further subjected to redeposition with chloroform, and a deposit was filtered by suction, and a filtrate was collected, to give NG2. Physical properties of NG2 are shown below.

Yield amount: 1.117 mg, Yield 74%.

ESI-MS (positive ion mode) m/z, found=171.0, calculated for [(M+H)+]=171.0.

found=193.1, calculated for [(M+Na)+]=193.0.

found=209.1, calculated for [(M+K)+]=209.0.

ESI-MS (negative ion mode) m/z, found=169.0, calculated for [(M–H)–]=518.0.

$^1$HNMR (400 MHz, CD3OD) δ7.73 (1H, s), 3.45 (2H, m), 3.30 (2H, s), 1.39 (9H, s)

(Synthesis Example 4) Synthesis of NG3

Scheme 8

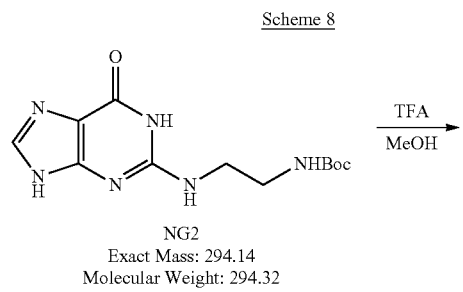

NG2
Exact Mass: 294.14
Molecular Weight: 294.32

NG3
Exact Mass: 194.09
Molecular Weight: 194.20

The NG2 (500 mg, $1.70 \times 10^{-5}$ mol) was suspended in methanol (3 mL), Trifluoroacetate (15 mL) was added and stirred at room temperature, to cause a reaction. After the reaction, the solvent in the mixture was distilled off under reduced pressure, suspended in Ether, and subjected to suction filtration, and the filtrate was collected, to give NG3. The physical properties of NG3 are shown below.

Yield amount: 467 mg, Yield: 89.1%

ESI-MS (positive ion mode) m/z, found=195.1, calculated for [(M+H)+]=195.1.

found=217.2, calculated for [(M+Na)+]=217.1.

found=233.0, calculated for [(M+K)+]=233.1.

$^1$HNMR (400 MHz, D20) 67.83 (1H, s), 3.55 (2H, t), 3.11 (2H, t)

(Synthesis Example 5) Synthesis of NG4

Scheme 9

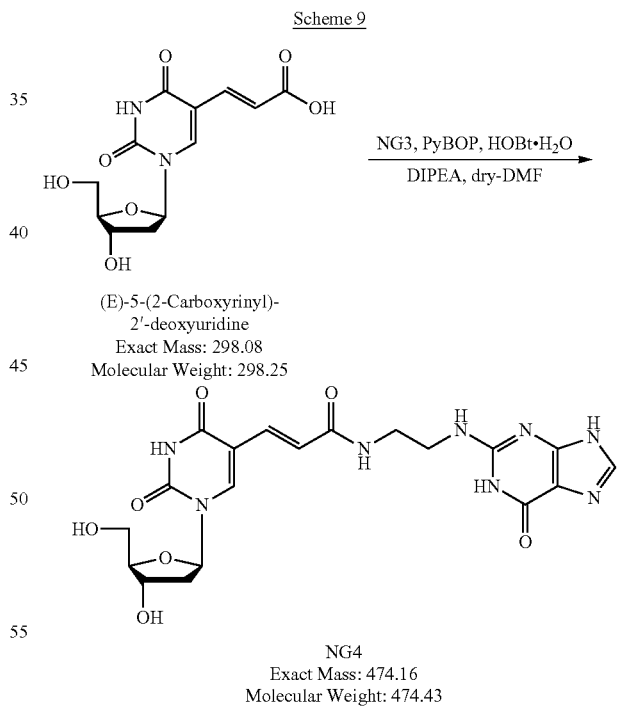

(E)-5-(2-Carboxyrinyl)-2'-deoxyuridine
Exact Mass: 298.08
Molecular Weight: 298.25

NG4
Exact Mass: 474.16
Molecular Weight: 474.43

(E)-5-(2-Carboxyrinyl)-2'-deoxyuridine (101 mg, $3.39 \times 10^{-4}$ mol) and a stirring bar were placed in a recovery flask A. The NG3 (171 mg, $4.12 \times 10^{-4}$ mol, 1.2 eq.) and a stirring bar were placed in a recovery flask B. The recovery flasks A and B were then dried in vacuo. Subsequently, the inside of the recovery flask A was replaced with Ar, and HOBt.H$_2$O (68 mg, $4.44 \times 10^{-4}$ mol, 1.3 eq.) and PyBOP® (hexafluorophosphoric acid (benzotriazole-1-yloxy)tripyrrolidinophosphonium, 229 mg, 4.40×10$^{-4}$ mol, 1.3 eq.) were then added, and the resultant mixture was dissolved in dry-DMF (N,N-dimethylformamide, 1 mL). Further, the inside of the recovery flask B was replaced with Ar, the NG3 was dissolved in DRY-dmf (0.5 mL). DIPEA (N,N-diisopropylethylamine, recovery flask A: 0.79 mL, 4.51×10$^{-5}$ mol, 13.3 eq.; recovery flask B: 0.79 mL, 4.51×10$^{-3}$ mol, 6.7 eq.) was added to each of the recovery flasks A and B, thereafter, the contents of the recovery flask B were rapidly added to the recovery flask A, stirred at room temperature, to cause a reaction. After the reaction, the solvent in the solution was distilled off under reduced pressure, and the resultant was suspended in CDCl$_3$ (deuterated chloroform). The obtained suspension was further sonicated and subjected to filtration. The obtained filtrate was recovered, suspended in MeOH, and sonicated, and then subjected to filtration. The obtained filtrate was collected, to give NG4. The physical properties of NG4 are shown below.

Yield amount: 147 mg, Yield: 91%

ESI-MS (positive ion mode) m/z, found=475.1, calculated for [(M+H)+]=475.2.

found=497.2, calculated for [(M+Na)+]=497.2.

ESI-MS (negative ion mode) m/z, found=473.1, calculated for [(M−H)−]=473.2.

$^1$HNMR (400 MHz, DMSO-d6) δ8.27 (1H, s), 8.20 (1H, s), 7.10 (1H, s), 7.05 (1H, s), 6.13 (1H, t), 5.25 (1H, d), 5.16 (1H, m), 4.09 (1H, m), 3.79 (1H, m), 3.60 (2H, m), 3.16 (2H, d), 2.14 (2H, m)

(Synthesis Example 6) Synthesis of NG5

The NG4 (101 mg, 2.13×10$^{-4}$ mol) was dried in vacuo, and the azeotropy between the NG4 and dry-Pyridine (30 mL) was then performed twice under Ar atmosphere. Subsequently, the azeotrope was suspended in dry-Trimethyl phosphate (21 mg), and Phosphoryl chloride (400 μL, 4.29×10$^{-5}$ mol, 20 eq.) was added under ice bath to the suspension and was then stirred for 2.5 hours. After the stirring, Phosphoryl chloride (200 μL, 2.15×10$^{-3}$ mol, 10 eq.) was added and was then stirred for 8.5 hours. After the stirring, cold water (10 ml) was added to quench, which was then stirred for 10 minutes. TEA (triethylamine, 2.7 mL, 1.94×10$^{-2}$ mol, 90 eq.) was then added, which was then stirred for 15 minutes. The solvent was then distilled off under reduced pressure, a crystallization was performed by Ether and MeCN (acetonitrile), and the obtained crystal was filtered, to collect a yellow precipitate. The obtained yellow precipitate was dissolved in water, purified by anion-exchange column chromatography, and freeze-dried, to give NG5. Physical properties of NG5 are shown below.

Yield amount: 41.49 μmol, Yield: 19.5%

ESI-MS (negative ion mode) m/z, found=553.1, calculated for [(M−H)−]=553.1

Scheme 10

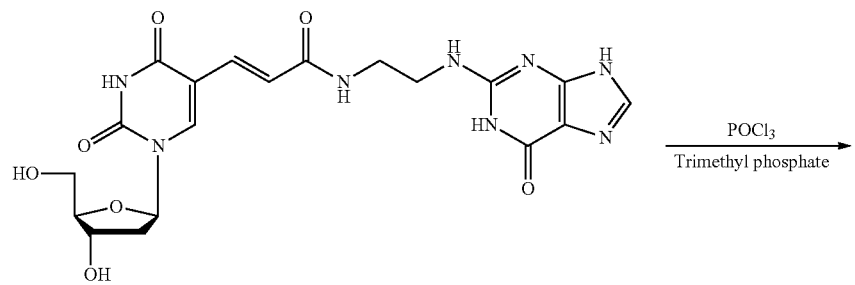

NG4
Exact Mass: 474.16
Molecular Weight: 474.43

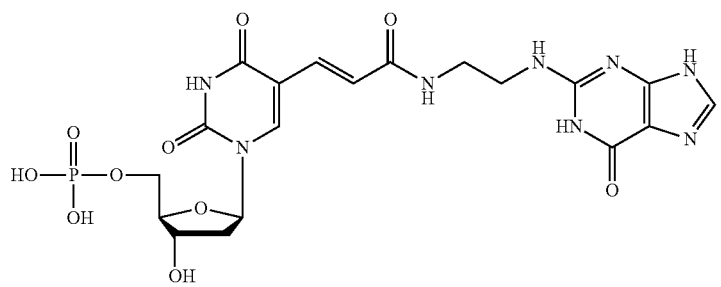

NG5
Exact Mass: 554.13
Molecular Weight: 554.41

(Synthesis Example 7) Synthesis of NG6

Scheme 11

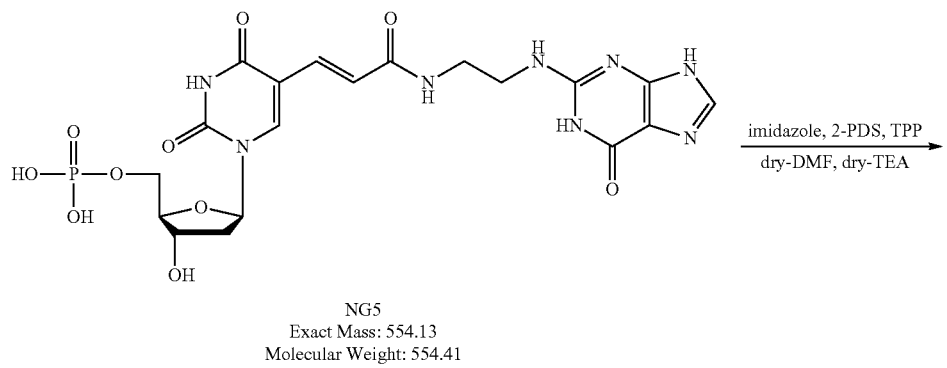

NG5
Exact Mass: 554.13
Molecular Weight: 554.41

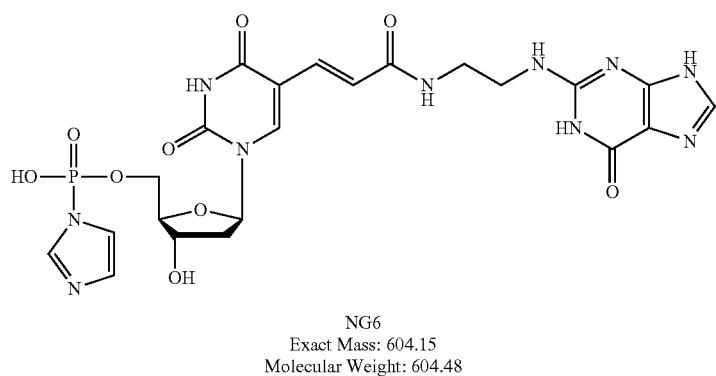

NG6
Exact Mass: 604.15
Molecular Weight: 604.48

The NG5 (78.65 μmol) was dried in vacuo, azeotropy between the NG5 and dry-Pyridine (5 mL) was thereafter caused three times, and the azeotrope was then further dried in vacuo overnight. After the drying, the atmosphere of this was replaced with Ar, this was then dissolved in dry-DMF (2 mL) and dry-TEA (72 μL, 5.19×10$^{-4}$ mol, 4 eq.), and Imidazole (24 mg, 3.53×10$^{-4}$ mol, 4 eq.), 2,2'-Dithiodipyridine (29 mg, 1.32×10$^{-4}$ mol, 1.6 eq.), and Triphenylphosphine (36 mg, 1.37×10$^{-4}$ mol, 1.6 eq.) were further added and stirred at room temperature. After 8 hours from the initiation of the stirring, the resultant reaction solution was added to a solution of Sodium perchlorate (97 mg, 7.92×10$^{-4}$ mol, 10 eq.) in dry-Acetone (18 mL), dry Ether (27 mL), and dry-TEA (2 mL), and allowed to stand at 4° C. for 30 minutes. The precipitate was decanted 5 times with dry-Ether (12 mL) and was thereafter dried in vacuo, to give NG6 as a crude.

Theoretical yield amount: 78.65 μmol (Synthesis Example 8) Synthesis of NG7

Scheme 12

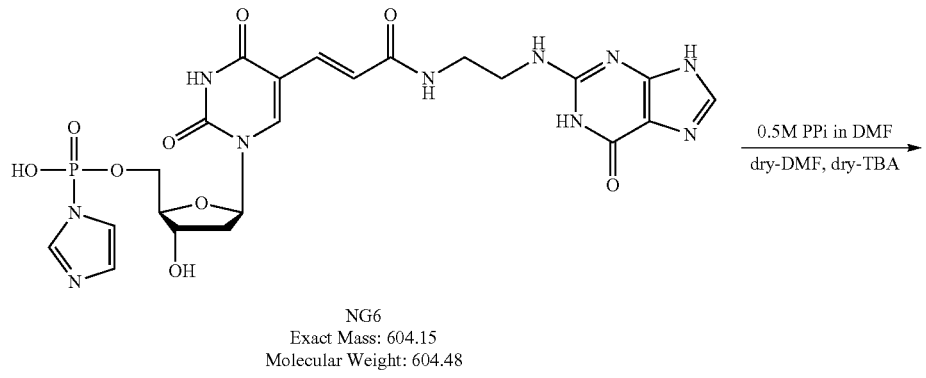

NG6
Exact Mass: 604.15
Molecular Weight: 604.48

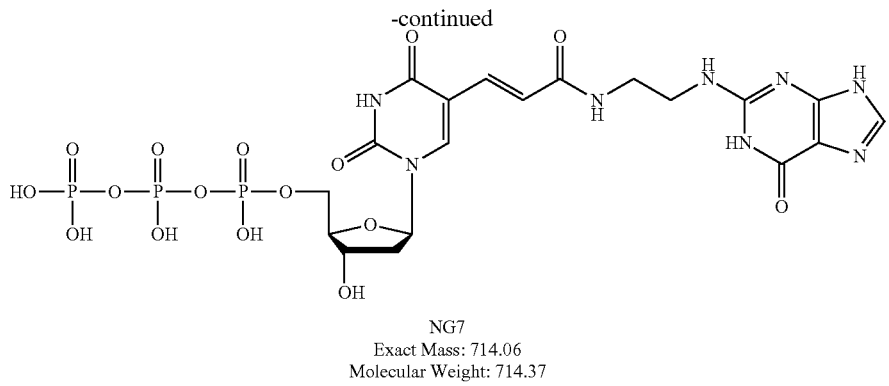

NG7
Exact Mass: 714.06
Molecular Weight: 714.37

The atmosphere of the vacuum-dried NG6 (78.65 μmol) was replaced with Ar, azeotropy between the NG6 and dry-Pyridine (5 mL) was then caused twice, and the azeotrope was suspended in dry-DMF (1 mL). Further, dry-n-Tributylamine (75 μL, 3.15×10$^{-4}$ mol, 4 eq.) and 0.5 mol/L n-Tributylamine pyrophosphate in DMF (0.8 μt, 3.93×10$^{-4}$ mol, 5 eq.) were added to the suspension and then stirred at room temperature. After 9 hours from the initiation of the stirring, a 1 mol/L TEAB (Triethylammonium bicarbonate) buffer (5 mL) was added and stirred for 30 minutes, and then the solvent was distilled off under reduced pressure. Water was added, an aqueous layer was separated with Ether twice, purified by anion-exchange column chromatography, and freeze-dried, to give NG7. Physical properties of NG7 are shown below.

Yield amount: 19.55 μmol, Yield: 24.9%
ESI-MS (negative ion mode) m/z, found=712.9, calculated for [(M–H)–]=713.1

Example 3

The present example examined the binding ability and a kinetic parameter of each of aptamers represented by SEQ ID NOs: 1 to 21 to sIgA by SPR.

(1) Aptamers

As aptamers of the examples, the following polynucleotides were synthesized. In the aptamers of SEQ ID NOs: 1 to 4 (hereinafter also referred to as "MK4 aptamers"), nucleotide residues containing underlined adeines in the following Table 3 are nucleotide residues represented by the chemical formula (1). In the aptamers of SEQ ID NOs: 8 to 12 and 16 to 21 (hereinafter also referred to as "KS9 aptamers"), nucleotide residues containing underlined thymines in the following Table 3 are nucleotide residues represented by the chemical formula (2). In the aptamers of SEQ ID NOs: 5 to 7 and 13 to 15 (hereinafter also referred to as "NG7 aptamers", nucleotide residues containing underlined thymines in the following Table 3 are nucleotide residues represented by the chemical formula (3).

TABLE 3

| SEQ ID NO: | Modified base | Base sequence |
|---|---|---|
| 1 | MK4 | 5'-GGTTTGGACGCAATCTCCCTAATCTACTACGATATCCAGATGGGAAGTGACCGTGAAACTACAATGGGCGGGCTTATC-3' |
| 2 | MK4 | 5'-GGTTTGGACGCAATCTCCCTAATCAGATGATATCGAGATGCGAAGCGACCGCATGAAACTACAATGGGCGGGCTTATC-3' |
| 3 | MK4 | 5'-GGTTTGGACGCAATCTCCCTAATCAAGCCACGGAGAGTCCGAGGTGACCATTAAGCAGGAAACTACAATGGGCGGGCTTA-3' |
| 4 | MK4 | 5'-GGTTTGGACGCAATCTCCCTAATCGATCTAGATGGTCTCGGGTATGGCTAGATAGAAACTACAATGGGCGGGCTTATC-3' |
| 5 | NG7 | 5'-GGTTTGGACGCAATCTCCCTAATCTGCTGATGTTTGTATTTCAAATTAGCCGCAGAAACTACAATGGGCGGGCTTATC-3' |
| 6 | NG7 | 5'-GGTTTGGACGCAATCTCCCTAATCTAAATAGATTTCACAGTGGATCCTTCAGAGGAAACTACAATGGGCGGGCTTATC-3' |
| 7 | NG7 | 5'-GGTTTGGACGCAATCTCCCTAATCAGACAATATTAGAGTGTTACCACCTGTGATGAAACTACAATGGGCGGGCTTATC-3' |
| 8 | KS9 | 5'-GGTTTGGACGCAATCTCCCTAATCGTATATCAAGCAGATGTGTTCACTTGGGGAGAAACTACAATGGGCGGGCTTATC-3' |
| 9 | KS9 | 5'-GGTTTGGACGCAATCTCCCTAATCAAAGATATGCTAAGATAGATAGTTTGGCTTGAAACTACAATGGGCGGGCTTATC-3' |
| 10 | KS9 | 5'-GGTTTGGACGCAATCTCCCTAATCACCTGTACTGGTTATTATGCCTGCCAACATGAAACTACAATGGGCGGGCTTATC-3' |
| 11 | KS9 | 5'-GGTTTGGACGCAATCTCCCTAATCTTTATACGTATGGACTTAGGCTTTGTTATAGAAACTACAATGGGCGGGCTTATC-3' |
| 12 | KS9 | 5'-GGTTTGGACGCAATCTCCCTAATCCTATCTGTTTTATCAATTGTAGCAAGTTATGAAACTACAATGGGCGGGCTTATC-3' |
| 13 | NG7 | 5'-GGTTTGGACGCAATCTCCCTAATCTGCTGATGTTTGTATTTCAAATTAGCCGCAG-3' |
| 14 | NG7 | 5'-GCAATCTCCCTAATCTGCTGATGTTTGTATTTCAAATTAGCCGCAG-3' |
| 15 | NG7 | 5'-GCAATCTCCCTAATCTGCTGATGTTTGTATTTCAAATTAGC-3' |

TABLE 3-continued

| SEQ ID NO: | Modified base | Base sequence |
|---|---|---|
| 16 | KS9 | 5'-GGTTTGGACGCAATCTCCCTAATCGTATATCAAGCAGATGTGTTCACTTGGGGAG-3' |
| 17 | KS9 | 5'-GCAATCTCCCTAATCGTATATCAAGCAGATGTGTTCACTTGGGGAG-3' |
| 18 | KS9 | 5'-GGTTTGGACGCAATCTCCCTAATCAAAGATATGCTAAGATAGATAGTTTGGCTTG-3' |
| 19 | KS9 | 5'-GCAATCTCCCTAATCAAAGATATGCTAAGATAGATAGTTTGGCTTG-3' |
| 20 | KS9 | 5'-GGTTTGGACGCAATCTCCCTAATCTTTATACGTATGGACTTAGGCTTTGTTATAGAAAC-3' |
| 21 | KS9 | 5'-GCAATCTCCCTAATCTTTATACGTATGGACTTAGGCTTTGTTATAGAAAC-3' |

To the 3' end of each of the MK4 aptamers, 20-mer polydeoxythymine (poly[dT]) was added. Each of the thus-obtained poly(dT)-added aptamers was used in SPR to be described below. To the 3' end of each of the KS9 aptamers and the NG7 aptamers, 20-mer polydeoxyadenine (poly [dA]) was added. Each of the thus-obtained poly(dA)-added aptamers was used in SPR to be described below.

(2) Specimen

Commercially available human sIgA (IgA (Secretory), Human, manufactured by MP Biomedicals, LLC-Cappel Products, Catalog No.: #55905) was used as a specimen in the following tests.

(3) Analysis of Binding Ability by SPR

The analysis of the binding ability was carried out using a ProteON XPR36 (BioRad) in accordance with its instructions for use.

First, as a sensor chip designed specifically for the ProteON, a streptavidin-immobilized chip (trade name: ProteOn NLC Sensor Chip, BioRad) was set in the ProteON XPR36. Biotinylated poly(dA) at 5 μmol/L was injected to a flow cell of the sensor chip using ultrapure water (DDW), and the binding was allowed to proceed until the signal intensity (RU: Resonance Unit) reached about 900 RU. The biotinylated poly(dA) was prepared by biotinylating the 5' end of 20-mer deoxyadenosine. Then, the poly(dT)-added MK4 aptamer at 200 nmol/L was injected to the flow cell of the chip using an SPR buffer at a flow rate of 25 μL/min for 80 seconds, and the binding was allowed to proceed until the signal intensity reached about 800 RU. This result, which corresponds to the signal indicating the amount of the aptamer immobilized on the sensor chip, is referred to as an "aptamer immobilization measured value (A)". Subsequently, the specimen was injected using the SPR buffer at a flow rate of 50 μL/min for 120 seconds, followed by washing performed by flowing the SPR buffer under the same conditions for 300 seconds. The concentration of the human sIgA in the specimen was set to 400 nmol/L. Signal intensity measurement was performed concurrently with the injection of the specimen and the washing with the SPR buffer. With 0 seconds being the start of the injection, the mean value of signal intensities from 115 seconds to 125 seconds was determined. This result, which corresponds to the signal indicating the binding amount between the aptamer and the protein, is referred to as a "protein binding measured value (B)". Then, the value (B/A) obtained by dividing the protein binding measured value (B) by the aptamer immobilization measured value (A) was determined as a relative value (Relative Unit). The KS9 aptamer and the NG7 aptamer were subjected to the measurement in the same manner as described above except that biotinylated poly dT prepared by biotinylating the 5' end of 20-mer deoxythymidine is used as a substitute for the biotinylated poly dA, and the KS9 aptamer or the NG7 aptamer was used as a substitute for the MK4 aptamer. Further, in Comparative Examples 3-1 and 3-2, the signal intensity was measured in the same manner as described above except that a negative-control nucleic acid molecule (SEQ ID NO: 22) exhibiting no binding properties to sIgA is used as a substitute for the MK4 aptamer in Comparative Example 3-1, and a specimen containing BSA (Bovine Serum Albumin, manufactured by SIGMA, Catalog No.: #A7906) was used as a substitute for the human sIgA in Comparative Example 3-2.

Negative-control nucleic acid molecules (N30-0 pool)

(SEQ ID NO: 22)
5'-GGTAACGCCCAGTCTAGGTCATTTG-(N)$_{30}$-GTTACGGGAGCCTGC

ACTTAATG-3'

The composition of the SPR buffer was as follows: 40 mmol/L HEPES, 125 mmol/L NaCl, 5 mmol/L KCl, 1 mmol/L MgCl$_2$, and 0.01% Tween® 20. The pH of the SPR buffer was set to 7.4.

FIGS. 1A to 1F show the results of binding between each aptamer and sIgA. FIGS. 1A to 1F are graphs showing the binding ability of the aptamers to sIgA. In FIG. 1, the horizontal axis indicates the elapsed time after injection of the specimen, and the vertical axis indicates the relative unit (RU) of binding affinity. As shown in FIGS. 1A to 1F, all of the aptamers bind to sIgA.

Then, FIGS. 2A to 2D show values (B/A) each obtained by dividing the protein binding measured value (B) by the aptamer immobilization measured value (A) as the results of relative values (relative units). FIGS. 2A to 2D are graphs showing the relative units (RU) of the binding amounts of the respective aptamers to sIgA. In FIG. 2, the horizontal axis indicates the type of the aptamer, and the vertical axis indicates the relative value. As shown in FIGS. 2A to 2D, binding was not found in Comparative Example 3-2 using BSA. Moreover, binding to sIgA was not found in Comparative Example 3-1 using the negative control nucleic acid molecule. In contrast, all of the aptamers were bound to sIgA. In particular, nucleic acid molecules of SEQ ID NOs: 15 and 21 exhibited excellent binding properties.

(4) Measurement of Dissociation Constant

The relative values (RU) of the binding amounts were measured in the same manner as described in the item (3) above except that the concentration of sIgA in the respective specimens were 12.5, 25, 50, 100, or 200 nmol/L. Then, based on the relative values of the binding amounts, the dissociation constants of the respective sIgA-binding nucleic acid molecules and the sIgA were calculated. The results obtained are shown in Table 4 below. As shown in Table 4 below, the dissociation constants of all of the aptamers were 37.7 nM or less. In particular, the nucleic acid molecules of SEQ ID NOs: 2, 3, 9, 11, 15, 19, and 21 were found to have dissociation constants of 8 nM or less and to have excellent binding abilities to sIgA.

TABLE 4

| SEQ ID NO: | Dissociation constant(Kd (nM)) |
|---|---|
| 1 | 8.6 |
| 2 | 7.6 |
| 3 | 7.6 |
| 4 | 17.4 |
| 5 | 11.8 |
| 6 | 11.6 |
| 7 | 37.7 |
| 8 | 10 |
| 9 | 4.8 |
| 10 | 30.2 |
| 11 | 1.3 |
| 12 | 9 |
| 14 | 10 |
| 15 | 2.59 |
| 17 | 12.9 |
| 19 | 8 |
| 21 | 2.1 |

(5) Determination of Cross-Reactivity

The relative values of the binding amounts were determined in the same manner as in the item (3) above except that the aptamers of SEQ ID NOs: 3, 5, and 9 were used, and a specimen containing sIgA, human IgG-Fc (Comparative Example 3-3, manufactured by BETHYL, Catalog No.: P-80-104), unlabeled human IgG (Comparative Example 3-4, manufactured by BECKMAN COULTER, Catalog No.: 731696), unlabeled human IgG-Fc (Comparative Example 3-5, manufactured by BECKMAN COULTER, Catalog No.: 731703), or human IgG1κ (Comparative Example 3-6, manufactured by Southern Biotech, Catalog No.: 0151K-01) to have 400 nmol/L was used as a specimen.

Figure 3:
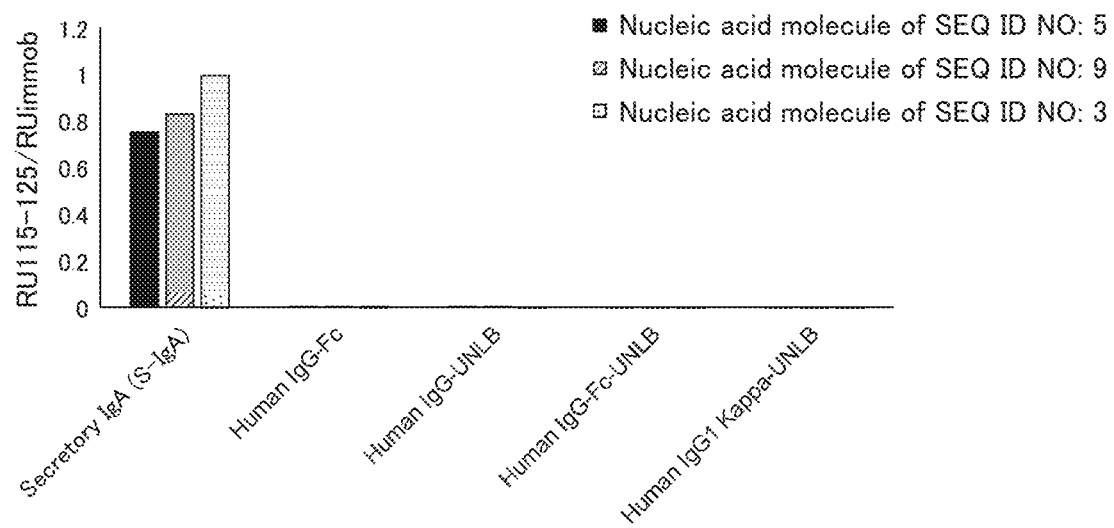
FIG. 3 is a graph showing the relative values of the binding amounts of the aptamers of Example 3.

The results obtained are shown in FIG. 3. FIG. 3 is a graph showing the relative values of the binding amounts. In FIG. 3, the horizontal axis indicates the type of the specimen, and the vertical axis indicates the relative value (RU) of the binding amount. As shown in Table 3 below, none of the aptamers is bound to immunoglobulins other than sIgA. From these results, it was found that the nucleic acid molecules of the present invention are specific to sIgA.

Example 4

The present example examined the binding ability of the aptamers of SEQ ID NOs: 5, 9, and 11 to sIgA by a pull-down assay using magnetic beads.

(1) Aptamer-Bound Beads

SA beads (Invitrogen Corporation, trade name: MyOne-SA C1), which are magnetic beads having streptavidin (SA) bound to their surfaces, were provided, and the aptamer of SEQ ID NO: 5, 9, or 11 was caused to bind to the SA beads to prepare aptamer-bound beads. More specifically, the aptamer-bound beads were prepared in the following manner. First, a complementary strand 100% complementary to the aptamer was prepared. On the other hand, a 5' region sequence (SEQ ID NO: 23, 5'-GGATACCT-TAACGCCGCCTATTG-3') of the aptamer was provided, and the 5' end thereof was biotinylated to prepare a biotinylated primer. Then, amplification by PCR was performed using the biotinylated primer with the complementary strand as a template, whereby the aptamer with the 5' end thereof being biotinylated was synthesized. A double strand composed of the synthesized aptamer and the complementary strand was reacted with the SA beads, thereby causing biotin in the double strand to bind to avidin in the SA beads. Subsequently, by an alkali treatment of the complexes of the double strands and the SA beads with NaOH, each double strand was dissociated to remove the complementary strand. Through the above-described process, the aptamer-bound beads, which are the SA beads having the biotinylated aptamers bound thereto via biotin-avidin binding, were prepared.

(2) Specimen

5 μg of human sIgA or Human saliva was used as a specimen in an experiment to be described below.

(3) Pull-Down Assay

The aptamer-bound beads (final concentration: 10 mg/mL) and the specimen (final concentration of sIgA: 50 μg/mL, final concentration of saliva: 90%) were mixed together in an SB1T buffer solution (40 mmol/L HEPES, 125 mmol/L NaCl, 5 mmol/L KCl, 1 mmol/L $MgCl_2$, and 0.01% Tween® 20, pH 7.4). This reaction solution was allowed to react at room temperature for 30 minutes. The reaction solution was centrifuged to collect the beads, and the beads were subjected to centrifugal washing with the SB1T buffer solution three times. In the case where the aptamer has bound to sIgA, the beads carry the sIgA bound thereto via the aptamer. Thus, the sIgA was released from the beads by mixing the beads in an SDS buffer solution and heat-treating the SDS buffer solution at 95° C. for 10 minutes. Then, the beads were removed from the SDS buffer solution after the heat treatment, and the SDS buffer solution was subjected to SDS-PAGE using a PAGEL (C520L, ATTO Corporation). As a buffer for electrophoresis, the SDS buffer was used. The composition of the SDS buffer was as follows: 25 mmol/L Tris, 192 mmol/L glycine, and 0.1% SDS.

Next, the gel after being subjected to the SDS-PAGE was stained using a GelCode Blue Stain Reagent (Thermo SCIENTIFIC). As a molecular-weight marker, a Bench Mark Protein Ladder (Invitrogen Corporation) was used. Further, as a control 1, SDS-PAGE and detection were carried out in the same manner, except that, instead of the aptamer-bound beads, the SA beads having the biotinylated primer bound thereto were used. Further, as a control 2, SDS-PAGE and detection were carried out with respect to the human sIgA.

Figure 4A:
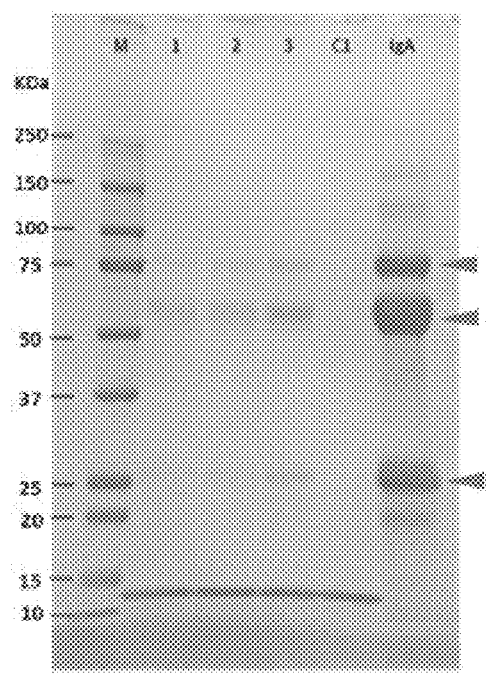
FIGS. 4A and 4B are photographs showing the results of SDS-PAGE in Example 4.
Figure 4B:
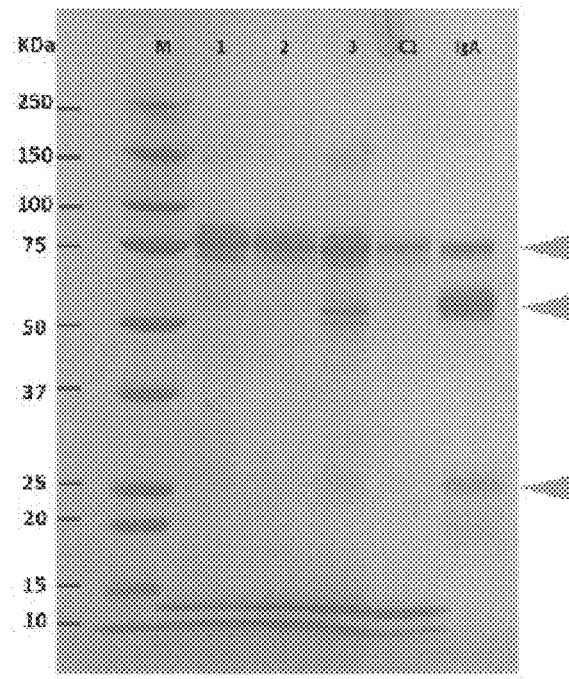

The results obtained are shown in FIG. 4. FIGS. 4A and 4B are photographs showing the results of the SDS-PAGE with respect to the proteins released from the aptamer-bound beads. FIG. 4A shows the result obtained by using a specimen containing sIgA, and FIG. 4B shows the result obtained by using saliva. In FIGS. 4A and 4B, the molecular weight is shown on the left side of the photograph, Lane M shows the molecular-weight marker (M), Lane 1 shows the result obtained when the aptamer-bound beads having the aptamer of SEQ ID NO: 5 bound thereto were used, Lane 2 shows the result obtained when the aptamer-bound beads having the aptamer of SEQ ID NO: 9 bound thereto were used, Lane 3 shows the result obtained when the aptamer-bound beads having the aptamer of SEQ ID NO: 11 bound thereto were used, Lane C1 shows the result obtained when the SA beads having the primer bound thereto were used, and Lane IgA shows the result of human sIgA.

As can be seen from FIGS. 4A and 4B, in Lanes 1 to 3 showing the result obtained when the aptamer-bound beads were used, the band was observed at the same site as in Lane IgA showing the result obtained when the sIgA was used (see the bands indicated with the arrows in FIGS. 4A and 4B). On the other hand, when the primer-bound beads were used, the band was not observed at the same site as when the sIgA was used.

From these results, it was found that the aptamer of the present invention exhibits binding properties to the human sIgA.

Although the present invention is described above with reference to embodiments and examples, the present invention is not limited thereto. Various modifications can be made within the scope of the present invention which can be understood by those skilled in the art.

The present application is based upon and claims the benefit of priority from Japanese patent application No. 2016-180892, filed on Sep. 15, 2016, and the entire disclosure of which is incorporated herein its entirety by reference.

INDUSTRIAL APPLICABILITY

The sIgA-binding nucleic acid molecule of the present invention can bind to sIgA with the above-described dissociation constant. Thus, the sIgA-binding nucleic acid molecule of the present invention can detect sIgA in a specimen with high accuracy on the basis of the presence or absence of the binding with the sIgA, for example. Therefore, it can be said that the sIgA-binding nucleic acid molecule of the present invention is a very useful tool for the detection of sIgA in the fields of preventive medicine, health care, diagnoses of infectious diseases, diagnoses of stress, and the like, for example.

[Sequence Listing] TF16064WO_ST25.txt

The invention claimed is:

1. A secretory immunoglobulin A (sIgA)-binding nucleic acid molecule that binds to sIgA with a dissociation constant of 37.7 nM or less,
   wherein the sIgA-binding nucleic acid molecule comprises the following polynucleotide (a) or (c):
   (a) a polynucleotide consisting of any of sequences of SEQ ID NOs: 1 to 12; and
   (c) a polynucleotide that consists of a sequence having at least 90% sequence identity to any of the sequences of the polynucleotide (a) and binds to the sIgA.

2. A secretory immunoglobulin A (sIgA)-binding nucleic acid molecule that binds to sIgA with a dissociation constant of 37.7 nM or less,
   wherein the sIgA-binding nucleic acid molecule comprises the following polynucleotide (a) or (c):
   (a) a following polynucleotide (a1), (a2), (a3) or (a4):
   (a1) a polynucleotide consisting of any of sequences of SEQ ID NOs: 13, 14, and 15;
   (a2) a polynucleotide consisting of either of sequences of SEQ ID NOs: 16 and 17;
   (a3) a polynucleotide consisting of either of sequences of SEQ ID NOs: 18 and 19; and
   (a4) a polynucleotide consisting of either of sequences of SEQ ID NOs: 20 and 21;
   (c) a polynucleotide that consists of a sequence having at least 90% sequence identity to any of the sequences of the polynucleotide (a) and binds to the sIgA.

3. The sIgA-binding nucleic acid molecule according to claim 1, wherein the sIgA-binding nucleic acid molecule comprises a modified base, which is a base modified with a modifying group.

4. The sIgA-binding nucleic acid molecule according to claim 3, wherein the modified base is a modified purine base, which is a purine base modified with a modifying group.

5. The sIgA-binding nucleic acid molecule according to claim 4, wherein the modifying group is an adenine residue.

6. The sIgA-binding nucleic acid molecule according to claim 3, wherein the modified base is a modified thymine, which is a thymine base modified with a modifying group.

7. The sIgA-binding nucleic acid molecule according to claim 6, wherein the modifying group is an adenine residue or a guanine residue.

8. The sIgA-binding nucleic acid molecule according to claim 1, wherein the polynucleotide is a DNA.

9. A secretory immunoglobulin A (sIgA) analysis sensor comprising: the sIgA-binding nucleic acid molecule according to claim 1.

10. A sIgA analysis method for analyzing sIgA, comprising the step of causing a specimen and a nucleic acid molecule to come into contact with each other to detect a secretory immunoglobulin A (sIgA) in the specimen, wherein
    the nucleic acid molecule is the sIgA-binding nucleic acid molecule according to claim 1, and
    in detection, the nucleic acid molecule is caused to bind to the sIgA in the specimen, and the sIgA in the specimen is detected by detecting the binding.

11. The sIgA analysis method according to claim 10, wherein the specimen is at least one selected from the group consisting of saliva, urine, plasma, and serum.

12. The sIgA-binding nucleic acid molecule according to claim 3, wherein a nucleotide residue containing a adenine in the polynucleotide (a) is a nucleotide residue containing a modified adenine, wherein
    the nucleotide residue containing a modified adenine is a represented by the following chemical formula (1)

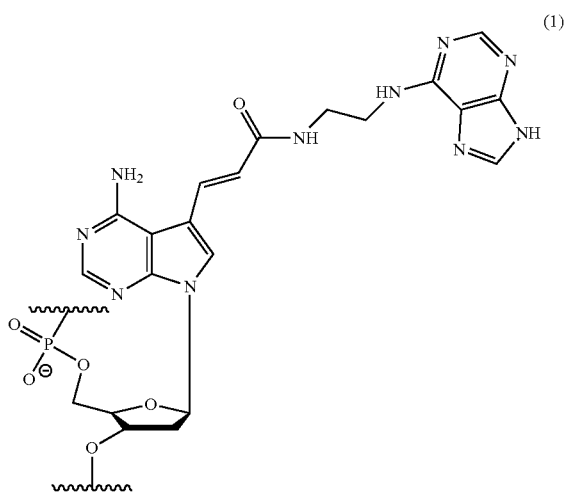

13. The sIgA-binding nucleic acid molecule according to claim 3, wherein a nucleotide residue containing a thymidine in the polynucleotide (a) is a nucleotide residue containing a modified thymidine, wherein the nucleotide residue containing the modified thymidine is represented by the following chemical formula (2) or (3)

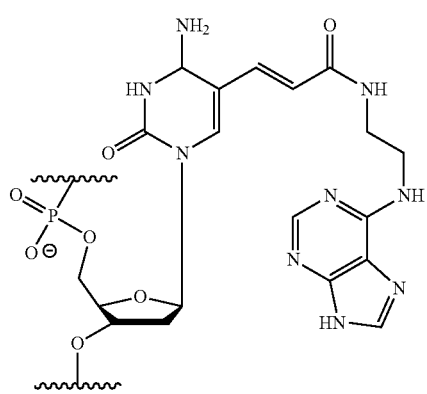

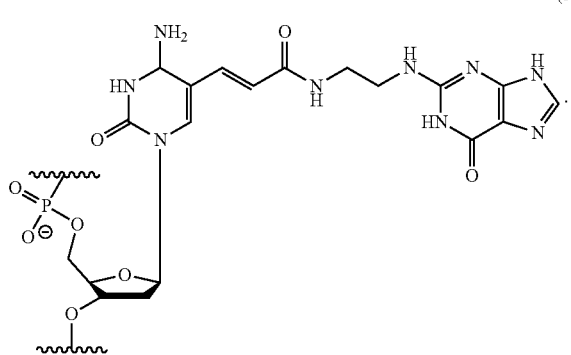

14. The sIgA-binding nucleic acid molecule according to claim 2, wherein the sIgA-binding nucleic acid molecule comprises a modified base, which is a base modified with a modifying group.

15. The sIgA-binding nucleic acid molecule according to claim 14, wherein a nucleotide residue containing a adenine in the polynucleotide (a) is a nucleotide residue containing a modified adenine, wherein the nucleotide residue containing a modified adenine is a represented by the following chemical formula (1)

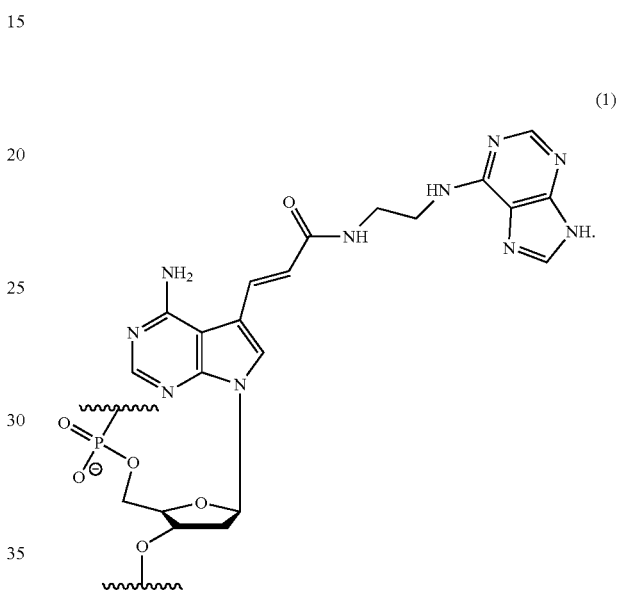

16. The sIgA-binding nucleic acid molecule according to claim 14, wherein a nucleotide residue containing a thymidine in the polynucleotide (a) is a nucleotide residue containing a modified thymidine, wherein the nucleotide residue containing the modified thymidine is represented by the following chemical formula (2) or (3)

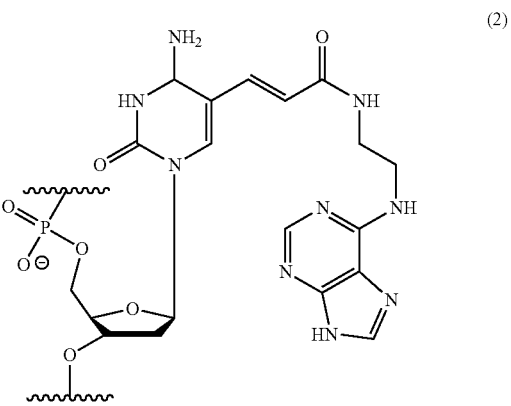

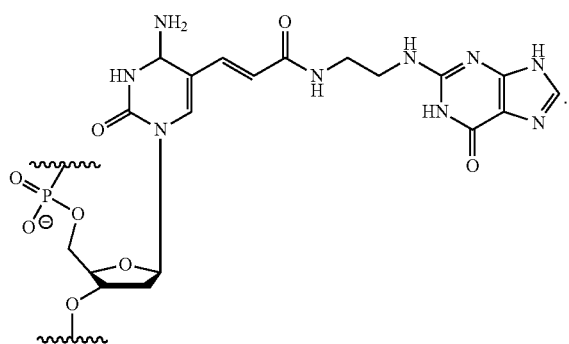

(3)

17. A secretory immunoglobulin A (sIgA) analysis sensor comprising: the sIgA-binding nucleic acid molecule according to claim 2.

18. A sIgA analysis method for analyzing sIgA, comprising the step of causing a specimen and a nucleic acid molecule to come into contact with each other to detect a secretory immunoglobulin A (sIgA) in the specimen, wherein
the nucleic acid molecule is the sIgA-binding nucleic acid molecule according to claim 2, and
in detection, the nucleic acid molecule is caused to bind to the sIgA in the specimen, and the sIgA in the specimen is detected by detecting the binding.

19. The sIgA analysis method according to claim 18, wherein the specimen is at least one selected from the group consisting of saliva, urine, plasma, and serum.

* * * * *

```
                            SEQUENCE LISTING

<160> NUMBER OF SEQ ID NOS: 23

<210> SEQ ID NO 1
    <211> LENGTH: 78
    <212> TYPE: DNA
    <213> ORGANISM: Artificial Sequence
    <220> FEATURE:
    <223> OTHER INFORMATION: Synthesized polynucleotide (sIgA binding
          nucleic acid molecule)

<400> SEQUENCE: 1
ggtttggacg caatctccct aatctactac gatatccaga tgggaagtga ccgtgaaact      60
acaatgggcg ggcttatc                                                    78

<210> SEQ ID NO 2
    <211> LENGTH: 78
    <212> TYPE: DNA
    <213> ORGANISM: Artificial Sequence
    <220> FEATURE:
    <223> OTHER INFORMATION: Synthesized polynucleotide (sIgA binding
          nucleic acid molecule)

<400> SEQUENCE: 2
ggtttggacg caatctccct aatcagatga tatcgagatg cgaagcgacc gcatgaaact      60
acaatgggcg ggcttatc                                                    78

<210> SEQ ID NO 3
    <211> LENGTH: 80
    <212> TYPE: DNA
    <213> ORGANISM: Artificial Sequence
    <220> FEATURE:
    <223> OTHER INFORMATION: Synthesized polynucleotide (sIgA binding
          nucleic acid molecule)

<400> SEQUENCE: 3
ggtttggacg caatctccct aatcaagcca cggagagtcc gaggtgacca ttaagcagga      60
aactacaatg ggcgggctta                                                  80

<210> SEQ ID NO 4
    <211> LENGTH: 78
    <212> TYPE: DNA
    <213> ORGANISM: Artificial Sequence
    <220> FEATURE:
    <223> OTHER INFORMATION: Synthesized polynucleotide (sIgA binding
          nucleic acid molecule)

<400> SEQUENCE: 4
```

```
ggtttggacg caatctccct aatcgatcta gatggtctcg ggtatggcta gatagaaact    60
acaatgggcg ggcttatc                                                 78

<210> SEQ ID NO 5
<211> LENGTH: 78
<212> TYPE: DNA
<213> ORGANISM: Artificial Sequence
<220> FEATURE:
<223> OTHER INFORMATION: Synthesized polynucleotide (sIgA binding
      nucleic acid molecule)

<400> SEQUENCE: 5
ggtttggacg caatctccct aatctgctga tgtttgtatt tcaaattagc cgcagaaact    60
acaatgggcg ggcttatc                                                 78

<210> SEQ ID NO 6
<211> LENGTH: 78
<212> TYPE: DNA
<213> ORGANISM: Artificial Sequence
<220> FEATURE:
<223> OTHER INFORMATION: Synthesized polynucleotide (sIgA binding
      nucleic acid molecule)

<400> SEQUENCE: 6
ggtttggacg caatctccct aatctaaata gatttcacag tggatccttc agaggaaact    60
acaatgggcg ggcttatc                                                 78

<210> SEQ ID NO 7
<211> LENGTH: 78
<212> TYPE: DNA
<213> ORGANISM: Artificial Sequence
<220> FEATURE:
<223> OTHER INFORMATION: Synthesized polynucleotide (sIgA binding
      nucleic acid molecule)

<400> SEQUENCE: 7
ggtttggacg caatctccct aatcagacaa tattagagtg ttaccacctg tgatgaaact    60
acaatgggcg ggcttatc                                                 78

<210> SEQ ID NO 8
<211> LENGTH: 78
<212> TYPE: DNA
<213> ORGANISM: Artificial Sequence
<220> FEATURE:
<223> OTHER INFORMATION: Synthesized polynucleotide (sIgA binding
      nucleic acid molecule)

<400> SEQUENCE: 8
ggtttggacg caatctccct aatcgtatat caagcagatg tgttcacttg gggagaaact    60
acaatgggcg ggcttatc                                                 78

<210> SEQ ID NO 9
<211> LENGTH: 78
<212> TYPE: DNA
<213> ORGANISM: Artificial Sequence
<220> FEATURE:
<223> OTHER INFORMATION: Synthesized polynucleotide (sIgA binding
      nucleic acid molecule)

<400> SEQUENCE: 9
ggtttggacg caatctccct aatcaaagat atgctaagat agatagtttg gcttgaaact    60
acaatgggcg ggcttatc                                                 78
```

<210> SEQ ID NO 10
<211> LENGTH: 78
<212> TYPE: DNA
<213> ORGANISM: Artificial Sequence
<220> FEATURE:
<223> OTHER INFORMATION: Synthesized polynucleotide (sIgA binding
      nucleic acid molecule)

<400> SEQUENCE: 10
ggtttggacg caatctccct aatcacctgt actggttatt atgcctgcca acatgaaact    60
acaatgggcg ggcttatc                                                  78

<210> SEQ ID NO 11
<211> LENGTH: 78
<212> TYPE: DNA
<213> ORGANISM: Artificial Sequence
<220> FEATURE:
<223> OTHER INFORMATION: Synthesized polynucleotide (sIgA binding
      nucleic acid molecule)

<400> SEQUENCE: 11
ggtttggacg caatctccct aatctttata cgtatggact taggctttgt tatagaaact    60
acaatgggcg ggcttatc                                                  78

<210> SEQ ID NO 12
<211> LENGTH: 78
<212> TYPE: DNA
<213> ORGANISM: Artificial Sequence
<220> FEATURE:
<223> OTHER INFORMATION: Synthesized polynucleotide (sIgA binding
      nucleic acid molecule)

<400> SEQUENCE: 12
ggtttggacg caatctccct aatcctatct gttttatcaa ttgtagcaag ttatgaaact    60
acaatgggcg ggcttatc                                                  78

<210> SEQ ID NO 13
<211> LENGTH: 55
<212> TYPE: DNA
<213> ORGANISM: Artificial Sequence
<220> FEATURE:
<223> OTHER INFORMATION: Synthesized polynucleotide (sIgA binding
      nucleic acid molecule)

<400> SEQUENCE: 13
ggtttggacg caatctccct aatctgctga tgtttgtatt tcaaattagc cgcag         55

<210> SEQ ID NO 14
<211> LENGTH: 46
<212> TYPE: DNA
<213> ORGANISM: Artificial Sequence
<220> FEATURE:
<223> OTHER INFORMATION: Synthesized polynucleotide (sIgA binding
      nucleic acid molecule)

<400> SEQUENCE: 14
gcaatctccc taatctgctg atgtttgtat ttcaaattag ccgcag                   46

<210> SEQ ID NO 15
<211> LENGTH: 41
<212> TYPE: DNA
<213> ORGANISM: Artificial Sequence
<220> FEATURE:
<223> OTHER INFORMATION: Synthesized polynucleotide (sIgA binding
      nucleic acid molecule)

```
<400> SEQUENCE: 15
gcaatctccc taatctgctg atgtttgtat ttcaaattag c                    41

<210> SEQ ID NO 16
<211> LENGTH: 55
<212> TYPE: DNA
<213> ORGANISM: Artificial Sequence
<220> FEATURE:
<223> OTHER INFORMATION: Synthesized polynucleotide (sIgA binding
      nucleic acid molecule)

<400> SEQUENCE: 16
ggtttggacg caatctccct aatcgtatat caagcagatg tgttcacttg gggag      55

<210> SEQ ID NO 17
<211> LENGTH: 46
<212> TYPE: DNA
<213> ORGANISM: Artificial Sequence
<220> FEATURE:
<223> OTHER INFORMATION: Synthesized polynucleotide (sIgA binding
      nucleic acid molecule)

<400> SEQUENCE: 17
gcaatctccc taatcgtata tcaagcagat gtgttcactt ggggag                46

<210> SEQ ID NO 18
<211> LENGTH: 55
<212> TYPE: DNA
<213> ORGANISM: Artificial Sequence
<220> FEATURE:
<223> OTHER INFORMATION: Synthesized polynucleotide (sIgA binding
      nucleic acid molecule)

<400> SEQUENCE: 18
ggtttggacg caatctccct aatcaaagat atgctaagat agatagtttg gcttg      55

<210> SEQ ID NO 19
<211> LENGTH: 46
<212> TYPE: DNA
<213> ORGANISM: Artificial Sequence
<220> FEATURE:
<223> OTHER INFORMATION: Synthesized polynucleotide (sIgA binding
      nucleic acid molecule)

<400> SEQUENCE: 19
gcaatctccc taatcaaaga tatgctaaga tagatagttt ggcttg                46

<210> SEQ ID NO 20
<211> LENGTH: 59
<212> TYPE: DNA
<213> ORGANISM: Artificial Sequence
<220> FEATURE:
<223> OTHER INFORMATION: Synthesized polynucleotide (sIgA binding
      nucleic acid molecule)

<400> SEQUENCE: 20
ggtttggacg caatctccct aatctttata cgtatggact taggctttgt tatagaaac  59

<210> SEQ ID NO 21
<211> LENGTH: 50
<212> TYPE: DNA
<213> ORGANISM: Artificial Sequence
<220> FEATURE:
<223> OTHER INFORMATION: Synthesized polynucleotide (sIgA binding
      nucleic acid molecule)
```

```
<400> SEQUENCE: 21
gcaatctccc taatctttat acgtatggac ttaggctttg ttatagaaac          50

<210> SEQ ID NO 22
<211> LENGTH: 78
<212> TYPE: DNA
<213> ORGANISM: Artificial Sequence
<220> FEATURE:
<223> OTHER INFORMATION: Synthesized polynucleotide (negative-control
      nucleic acid molecule)
<220> FEATURE:
<221> NAME/KEY: misc_feature
<222> LOCATION: (26)..(55)
<223> OTHER INFORMATION: n is a, c, g, or t

<400> SEQUENCE: 22
ggtaacgccc agtctaggtc atttgnnnnn nnnnnnnnnn nnnnnnnnnn nnnnngttac   60
gggagcctgc acttaatg                                                78

<210> SEQ ID NO 23
<211> LENGTH: 23
<212> TYPE: DNA
<213> ORGANISM: Artificial Sequence
<220> FEATURE:
<223> OTHER INFORMATION: Synthesized polynucleotide (5 prime region
      sequence)

<400> SEQUENCE: 23
ggatacctta acgccgccta ttg                                         23
```